(12) United States Patent
Silverman

(10) Patent No.: US 7,313,507 B2
(45) Date of Patent: Dec. 25, 2007

(54) SYSTEM AND METHOD FOR SPATIALLY PROFILING A DISTRIBUTION OF HYDROPHOBICITY OF A TRANSMEMBRANE PROTEIN

(75) Inventor: Benjamin David Silverman, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 627 days.

(21) Appl. No.: 10/653,091

(22) Filed: Sep. 3, 2003

(65) Prior Publication Data

US 2005/0049840 A1    Mar. 3, 2005

(51) Int. Cl.
*G06G 7/48* (2006.01)
(52) U.S. Cl. ............................. 703/11; 703/12; 702/19; 702/22
(58) Field of Classification Search ..................... None
See application file for complete search history.

(56) References Cited

OTHER PUBLICATIONS

Silverman, PNAS, vol. 98, No. 9, p. 4996-5001, 2001.*
Schirmer et al., Protein Science, vol. 2, p. 1361-1363, 1993.*
Gromiha et al., Int. J. of Peptide-Protein Research, vol. 48, p. 452-460, 1996.*
Brasseur, Jour. Biolo. Chem., vol. 263, No. 25, p. 12571-12575, 1988.*

\* cited by examiner

*Primary Examiner*—John S. Brusca
*Assistant Examiner*—Karlheinz R Skowronek
(74) *Attorney, Agent, or Firm*—Vazken Alexanian; McGinn IP Law Group, PLLC

(57) ABSTRACT

A system and method for spatially profiling a distribution of hydrophobicity of a transmembrane protein includes a scaler which generates scaled hydrophobicity values for the transmembrane protein, and a profiler which spatially profiles a hydrophobicity distribution for the transmembrane protein based on the scaled hydrophobicity values.

22 Claims, 16 Drawing Sheets

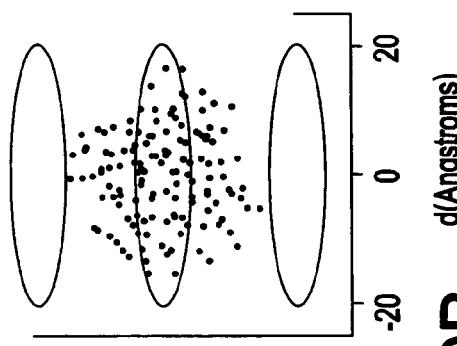
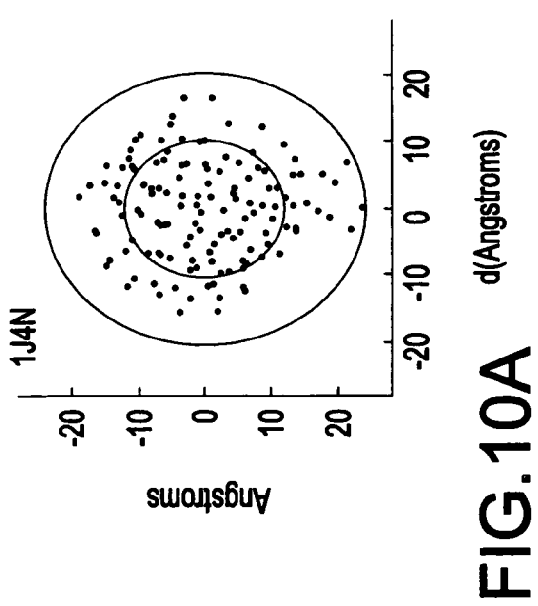
FIG.10A
FIG.10B
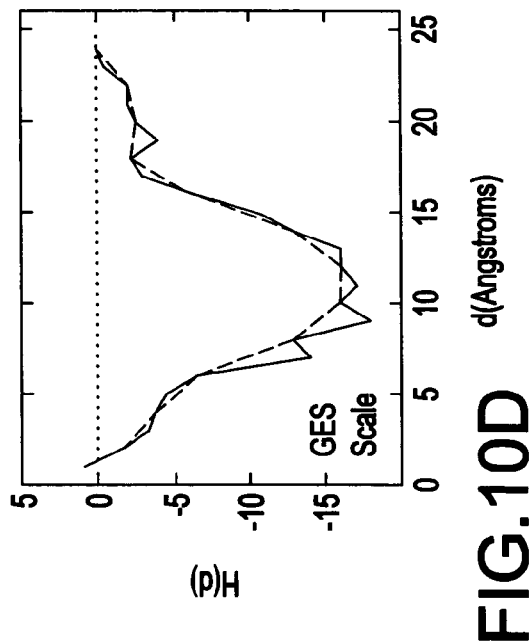
FIG.10D
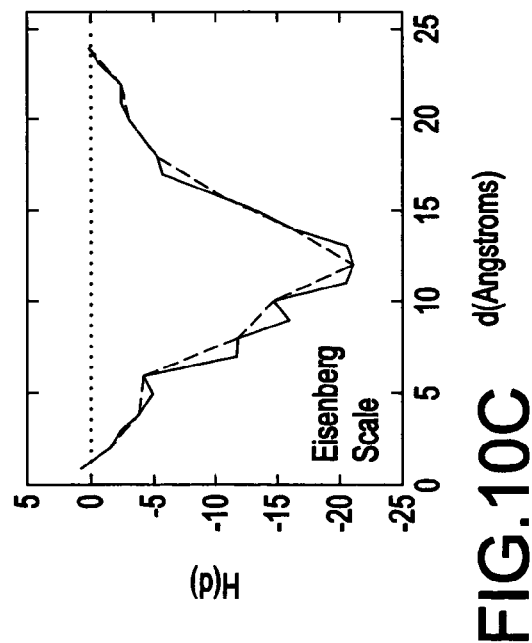
FIG.10C

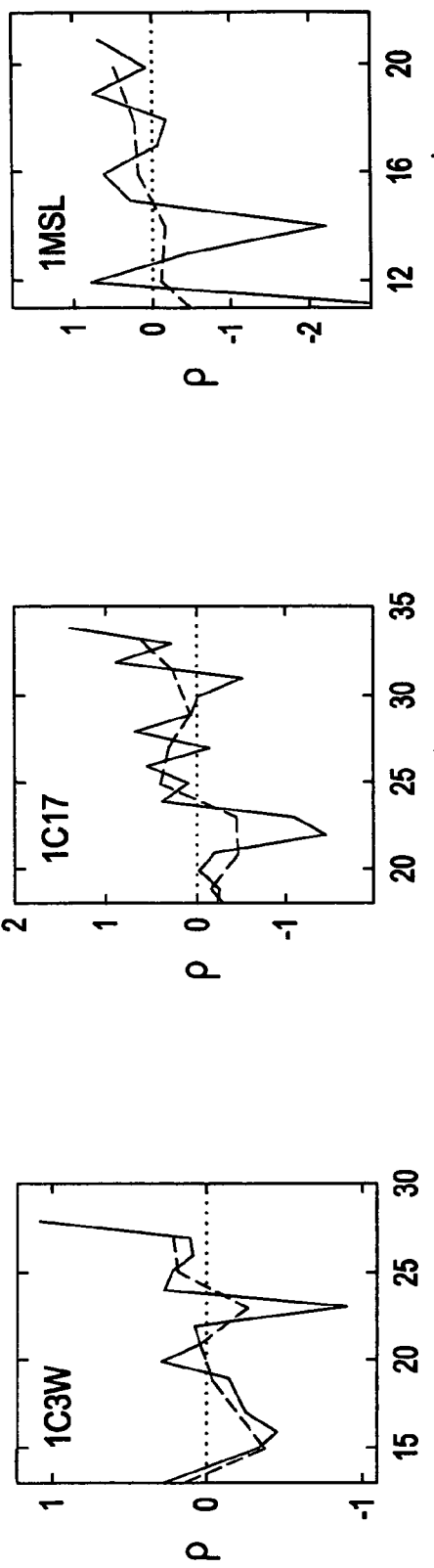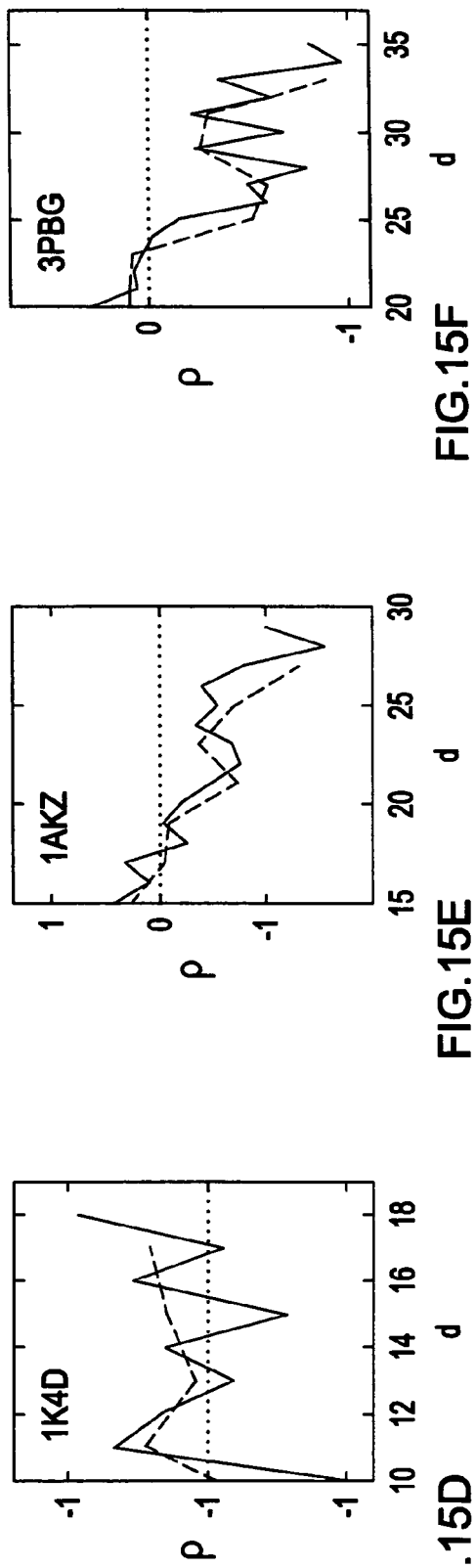
FIG.15A FIG.15B FIG.15C
FIG.15D FIG.15E FIG.15F

RESCALED EISENBERG AMINO ACID HYDROPHOBICITY SCALE

| AMINO ACID | 1C3W | 1C17 | 1MSL | 1K4D | 1AKZ | 3PBG |
|---|---|---|---|---|---|---|
| ARG | -3.98 | -7.85 | -4.89 | -4.08 | -2.61 | -2.65 |
| LYS | -2.49 | -5.40 | -3.31 | -2.70 | -1.55 | -1.57 |
| ASP | -1.63 | -4.00 | -2.41 | -1.90 | -0.94 | -0.95 |
| GLU | -1.56 | -3.88 | -2.33 | -1.84 | -0.89 | -0.90 |
| ASP | -1.45 | -3.70 | -2.21 | -1.74 | -0.81 | -0.82 |
| GLU | -1.40 | -3.63 | -2.17 | -1.69 | -0.78 | -0.79 |
| HIS | -0.90 | -2.81 | -1.64 | -1.23 | -0.42 | -0.43 |
| SER | -0.59 | -2.29 | -1.31 | -0.94 | -0.20 | -0.20 |
| THR | -0.41 | -2.00 | -1.12 | -0.77 | -0.07 | -0.07 |
| PRO | -0.16 | -1.59 | -0.85 | -0.54 | 0.11 | 0.11 |
| TYR | 0.05 | -1.25 | -0.64 | -0.36 | 0.26 | 0.26 |
| CYS | 0.09 | -1.18 | -0.59 | -0.31 | 0.29 | 0.29 |
| GLY | 0.36 | -0.74 | -0.30 | -0.06 | 0.48 | 0.49 |
| ALA | 0.57 | -0.40 | -0.09 | 0.12 | 0.63 | 0.64 |
| MET | 0.59 | -0.37 | -0.07 | 0.15 | 0.64 | 0.65 |
| TRP | 0.84 | 0.04 | 0.20 | 0.38 | 0.82 | 0.83 |
| LEU | 1.20 | 0.63 | 0.58 | 0.71 | 1.08 | 1.09 |
| VAL | 1.22 | 0.67 | 0.60 | 0.73 | 1.09 | 1.11 |
| PHE | 1.38 | 0.93 | 0.77 | 0.88 | 1.21 | 1.22 |
| ILE | 1.65 | 1.37 | 1.06 | 1.13 | 1.40 | 1.42 |

FIG. 16

SYSTEM AND METHOD FOR SPATIALLY PROFILING A DISTRIBUTION OF HYDROPHOBICITY OF A TRANSMEMBRANE PROTEIN

BACKGROUND OF THE INVENTION

1. Field of the Invention

The present invention relates to a system and method for spatially profiling a hydrophobicity distribution for a transmembrane protein, and more particularly, to a system for spatially profiling a hydrophobicity distribution for a transmembrane protein based on scaled hydrophobicity values for the transmembrane protein.

2. Description of the Related Art

The distribution of residue hydrophobicity from protein interior to exterior has been a subject of continued interest. The identification of the hydrophobic core of soluble globular proteins has provided a key feature relating an amino acid attribute to tertiary protein structure. Furthermore, a detailed relationship between the hydrophobic character of a local sequence of amino acids and variations of its proximity to the protein exterior has been described. The spatial segregation of residues, dependent upon amino acid hydrophobicity, has also assisted with validating predicted native protein structures, as well as with identifying the origin of nucleation sites during the initiation of protein folding.

While there has been a general consensus of opinion concerning the overall hydrophobic spatial distribution of the residues of soluble proteins, opinion concerning the hydrophobic distribution of the residues of transmembrane protein structures has had a more varied history. Early work had suggested that Bacteriorhodopsin was an "inside-out" protein. The terminology, "inside-out", referred to a reversed sense of the hydrophobic distribution within the lipid bilayer from that of soluble globular proteins, namely, that the interior was composed of hydrophilic residues and the exterior of hydrophobic residues. Apparently the "inside-out" model of membrane protein structure is no longer accepted.

Notwithstanding, a relatively recent calculation that utilizes solvent-lipid accessibility, as have prior investigations, and purports to discredit the "inside-out" hypothesis, actually attempts to discredit a more general hypothesis, namely, that residues of greater hydrophobic character have a statistical preference to reside nearer the protein lipid interface. This latter hypothesis is independent of the residue character of the protein interior, being a statement of variations about the mean or average residue hydrophobicity of the distribution, whatever that distribution might be.

However, conventional systems and methods do not attempt to profile the distribution of hydrophobicity of transmembrane proteins. Thus, conventional systems and methods do not enable a determination of the spatial distribution of hydrophobicity within the interior of a structure, where the residue solvent-lipid exposure either vanishes or is minimal.

SUMMARY OF THE INVENTION

In view of the foregoing and other problems, disadvantages, and drawbacks of the aforementioned assemblies and methods, it is a purpose of the exemplary aspects of the present invention to provide a system and method for spatially profiling a hydrophobicity distribution for a transmembrane protein.

A hallmark of soluble globular protein tertiary structure is a hydrophobic core and a protein exterior populated predominantly by hydrophilic residues. Recent hydrophobic moment profiling of the spatial distribution of thirty globular proteins of diverse size and structure had revealed features of this distribution that were comparable. Analogous profiling of the hydrophobicity distribution of the $\alpha$-helical buried bundles of several transmembrane proteins, as the lipid/protein interface is approached from within the bilayer, reveals spatial hydrophobicity profiles that contrast with those obtained for the soluble proteins. The calculations enabling relative changes of hydrophobicity to be simply identified over the entire spatial extent of the multimer within the lipid bilayer, show the accumulated zero-order moments of the bundles to be mainly inverted with respect to that found for the soluble proteins. This indicates a statistical increase in the average residue hydrophobic content as the lipid bilayer is approached.

This result differs from that of a relatively recent calculation and qualitatively agrees with earlier calculations involving lipid exposed and buried residues of the $\alpha$-helices of transmembrane proteins. Spatial profiling, over the entire spatial extent of the multimer with scaled values of residue hydrophobicity, further provides information that is not available from calculations utilizing lipid exposure alone.

An exemplary aspect of the present invention includes a system for spatially profiling a hydrophobicity distribution for a transmembrane protein (e.g., a transmembrane protein formed in a lipid bilayer). The system includes a scaler which generates scaled hydrophobicity values for the transmembrane protein, and a profiler which spatially profiles a hydrophobicity distribution for the transmembrane protein based on the scaled hydrophobicity values. The system may also include a database which stores data pertaining to a structure of the transmembrane protein, and an input device for inputting and manipulating the data, and a display device (e.g., user interface) for viewing and manipulating data in the system.

Further, the scaled hydrophobicity values may include shifted and scaled hydrophobicity values of residue hydrophobicity. More specifically, the scaled hydrophobicity values may be derived from data pertaining to a structure of the transmembrane protein.

In addition, the profiler may spatially profile the hydrophobicity distribution over a spatial extent of the transmembrane protein. Further, the profiler may include an identifier which identifies a residue external to the membrane, using at least one of hydrophobicity sliding window analysis and visual inspection. The profiler may further include a residue remover which removes the residue to obtain a truncated structure, and a calculator which calculates a residue centroid of each residue side-chain of the truncated structure to obtain a geometric center of a distribution of the residue centroids. In addition, the calculator may calculate a hydrophobicity profile about an axis through the geometric center and normal to a plane of the membrane, using a predetermined profiling geometry. Further, the profiler and scaler, and any components of the features may be integrally formed as one or more processors operatively coupled to form the present invention.

For example, the predetermined profiling geometry may be selected to approximate an overall external shape of the transmembrane protein within a lipid bilayer, and generate a series of nested shapes consistent with the profiling geometry. Further, the series of nested shapes may provide contours about the axis that correlate with a lipid exposure for the residues proximate to a protein/lipid boundary. For example, the structure of the transmembrane protein may be asymmetrical about the axis, and the predetermined profiling geometry may include an elliptical cylinder.

Further, the scaler may scale the hydrophobicity values to obtain the scaled hydrophobicity values, using a scale that similarly segregates amino acid values of hydrophobicity into a polar, polar uncharged and polar charged residues. The scaler may also shift the scaled hydrophobicity values to provide shifted and scaled values having a value of zero hydrophobicity when a predetermined number of residues of each truncated structure are collected, the shifted and scaled values being scaled to provide a standard deviation of unity for each truncated structure.

Further, the profiler may accumulate the shifted and scaled values of residue hydrophobicity as a function of an increasing size of each nested shape of a profiling geometry until a largest shape encapsulates a predetermined number of the residues, to generate an accumulated spatial distribution of residue hydrophobicity given by a function H(d) which is a sum of residue hydophobicity values within the circular, elliptical or conical cylinder of radius d. The profiler may, therefore, obtain a hydrophobicity profile by calculating the values of H(d).

For example, if H(d) increases, the average hydrophobic value of the residues collected over a shell of width one or more Angstroms is greater than the average value of residue hydrophobicity for the entire structure. However, if H(d) decreases, the average hydrophobic value of the residues collected over a shell of width one or more Angstroms is less than the average value of residue hydrophobicity for the entire structure.

Further, the accumulated spatial distribution may include a set of sequential values of accumulated residue hydrophobicity with increasing distance from a center of the structure to the protein/lipid interface within a bilayer, the set of sequential values comprising a zero-order moment profile of the residue hydrophobicity from the interior to the exterior of the structure.

Another exemplary aspect of the present invention includes a method of spatially profiling a hydrophobicity distribution for a transmembrane protein. The method includes scaling hydrophobicity values for the transmembrane protein to generate scaled hydrophobicity values, and spatially profiling a hydrophobicity distribution for the transmembrane protein based on the scaled hydrophobicity values.

Specifically, the spatially profiling may include identifying a residue external to the membrane, using hydrophobicity sliding window analysis and by visual inspection, removing the residue to obtain a truncated structure, calculating a residue centroid of each residue side-chain of the truncated structure to obtain a geometric center of a distribution of the residue centroid. and/or calculating a hydrophobicity profile about an axis through the geometric center and normal to the plane of the membrane, using a predetermined profiling geometry.

Further, scaling the hydrophobicity values may include scaling hydrophobicity values to obtain the scaled hydrophobicity values, using a scale that similarly segregates amino acid values of hydrophobicity into a polar, polar uncharged and polar charged residues. In addition, scaling the hydrophobicity values may further include shifting the scaled hydrophobicity values to provide shifted and scaled values having a value of zero hydrophobicity when a predetermined number of residues of each truncated structure are collected, the shifted and scaled values being scaled to provide a standard deviation of unity for each truncated structure.

Further, spatially profiling may further include accumulating the shifted and scaled values of residue hydrophobicity as a function of increasing size of each nested shape of the profiling geometry until a largest shape encapsulates a predetermined number of the residues, to generate an accumulated spatial distribution of residue hydrophobicity given by the function H(d) which is the sum of the values of residue hydophobicity within the circular, elliptical or conical cylinder of radius d. Spatially profiling may also include obtaining a hydrophobicity profile by calculating the values of H(d).

Another exemplary aspect of the present invention includes a programmable storage medium tangibly embodying a program of machine-readable instructions executable by a digital processing apparatus to perform the inventive method of spatially profiling a hydrophobicity distribution for a transmembrane protein.

Another exemplary aspect of the present invention includes a method of deploying computing infrastructure in which computer-readable code is integrated into a computing system, such that the code and the computing system combine to perform the inventive method of spatially profiling a hydrophobicity distribution for a transmembrane protein.

With its unique and novel features, the present invention provides a system and method which enables a determination of the spatial distribution of hydrophobicity over an entire multimeric extent, not only in the region proximate to the protein lipid interface.

BRIEF DESCRIPTION OF THE DRAWINGS

The foregoing and other exemplary aspects and advantages will be better understood from the following detailed description of the exemplary embodiments of the invention with reference to the drawings, in which:

FIGS. 10A-10D illustrate a distribution of residue centroids and hydophobicity profiles of the Aqp1 Water Channel, 1J4N, according to an exemplary embodiment of the present invention;

FIGS. 15A-15F illustrate the hydrophobicity density, $\rho(d)$, as a function of distance, d, from the protein interior of the four transmembrane bundles of, 1 C3W, 1C17, 1 MSL, 1 K4d and of the soluble proteins, 1AKZ and 3PBG, according to an exemplary embodiment of the present invention;

FIG. 16 provides Table 1 which lists the shifted and normalized values of amino acid hydrophobicity that had provided the values of the densities, $\rho(d)$;

DETAILED DESCRIPTION OF THE EMBODIMENTS OF THE INVENTION

Figure 1:
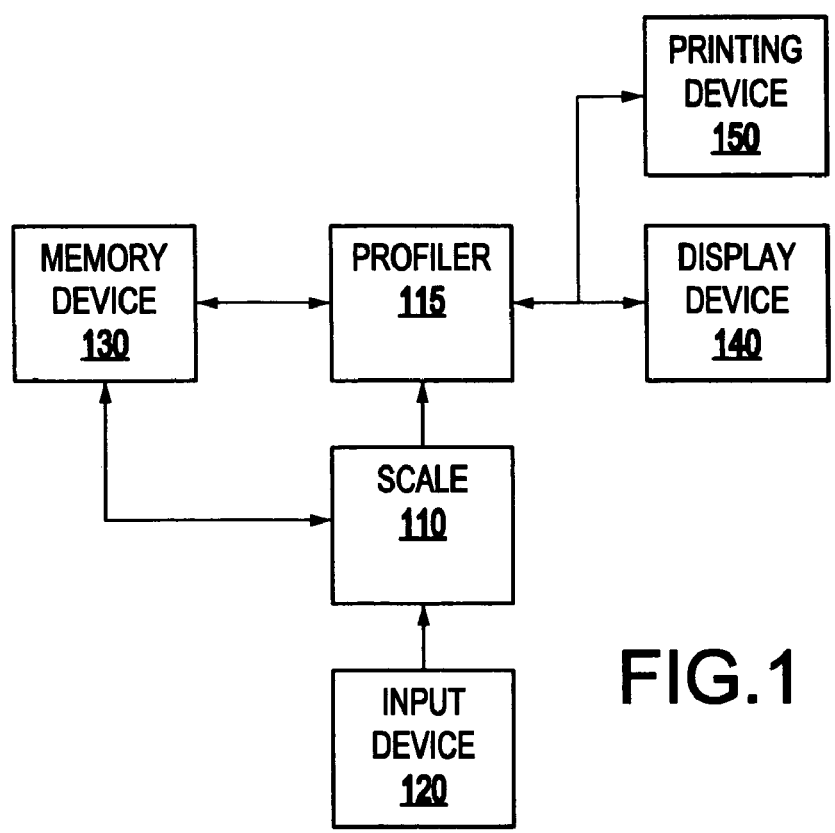
FIG. 1 illustrates a system 100 for spatially profiling a hydrophobicity distribution for a transmembrane protein, according to an exemplary embodiment of the present invention.

Referring now to the drawings, FIG. 1 illustrates a system 100 for spatially profiling the distribution of hydrophobicity of transmembrane proteins. As shown in FIG. 1, the system 100 includes a scaler 110 which generates scaled hydrophobicity values for the transmembrane protein, and a profiler 115 which spatially profiles a hydrophobicity distribution for the transmembrane protein based on the scaled hydrophobicity values (e.g., shifted and scaled hydrophobicity values) the transmembrane protein.

The system 100 may also include an input device 120 for inputting data (e.g., structural data) pertaining to the transmembrane protein. The system 100 may also include a memory device 130 (e.g., database) for storing data used by the system 100, and data generated by the system 100. The system 100 may also include a display device 140 which may be used to display the results of the calculations performed by the processor 110, and a printing device 150 which may be used to print those results.

Motivated by the problems of conventional systems and methods, the inventor investigated the distribution of residue hydrophobicity of several transmembrane proteins from a point of view which is different from conventional methods. The direct spatial profiling of the residue distribution of the multimeric protein structures was performed without reference to residue solvent-lipid accessibility. Profiling in this manner also enables a determination of the spatial distribution of hydrophobicity within the interior of the structure, where the residue solvent-lipid exposure either vanishes or is minimal.

A recent calculation examined the spatial distribution of the residue hydrophobicity of soluble globular proteins. It was shown that shifting the scale of residue hydrophobicity, such that the total residue hydrophobicity of each structure vanished, enabled variations of the spatial distribution of residue hydrophobicity about the mean of the distribution to be simply identified. It also enabled a comparison to be made between the hydrophobicity distributions of different proteins over their different length scales.

Such procedure is, therefore, appropriate for examining spatial variations of the hydrophobic content of the residues of transmembrane proteins. It not only addresses the question of the hydrophobic statistical preference of residues directly, but also provides information over the entire multimeric extent, not only in the region proximate to the protein lipid interface.

The hydrophobicity profiles of globular proteins had revealed two spatial regions delineating the hydrophobic core and hydrophilic exterior. The profiles of the multimers comprised of transmembrane $\alpha$-helices, while mainly inverted with respect to the profiles of the globular proteins, do not always exhibit such uniform delineation. The spatial profiling of structures about the normal to the plane of the lipid bilayer, yields features related to structural details within the interior of the helical bundle as well as features related to exterior local structural details that are not characteristic of the entire protein-lipid periphery.

On the other hand, the major fraction of residues that are proximate to the protein lipid interface for all of the $\alpha$-helical structures investigated were shown to exhibit a statistical increase in residue hydrophobic content as the interface is approached. The results, therefore, qualitatively agree with previous calculations involving surface exposed and buried residues. This increase in residue hydrophobic content, as the protein-lipid interface is approached is, however, more modest than the converse variation observed for the soluble globular proteins.

The inventor conducted experiments in which eleven transmembrane protein structures with a SCOP 'membrane all- $\alpha$ fold' classification were downloaded from the Protein Data Bank. The light-driven ion pump, Bacteriorhodopsin, 1C3W, and the photosynthetic reaction center, *Rhodobacter sphaeroides*, 1PCR, were chosen since they had been the subject of previous discussion focused on their spatial distribution of a polar and polar residues.

Three of the structures were chosen due to their symmetric, as well as diverse multimeric geometries. The gated mechanosensitive ion channel from *Mycobacterium tuberculosis*, 1MSL, was chosen due to its interestingly entwined multimeric cylindrical symmetry with helices that are canted significantly with respect to the surface of the lipid bilayer. The subunit C of the ATP synthase from *Escherichia coli*, 1

C 17, was chosen due to its cylindrically symmetric set of helices approximately perpendicular to the lipid bilayer. The potassium ion channel from *Streptomyces lividans*, 1K4D, was chosen due to the overall conical geometry of its membrane-spanning segment.

Six structures lacking symmetry about an axis normal to the plane of the bilayer were additionally chosen. The six are the Cytochrome-C Oxidase, 1EHK, the Aqp1 Water Channel, 1J4N, the Bacterial Abc Transporter, 1L7V, *E. Coli* Quinol-Fumarate Reductase, 1KF6, the Cytochrome Bc1 Complex, 1BE3, and the Photosynthetic Reaction Center: Photosystem I, 1JB0.

Prior to calculation, residues presumed to be external to the membrane were removed. These residues were identified by hydrophobicity sliding window analysis and by visual inspection. The final truncated protein structures were composed of a majority of α-helices with five turns or greater.

Figure 2:
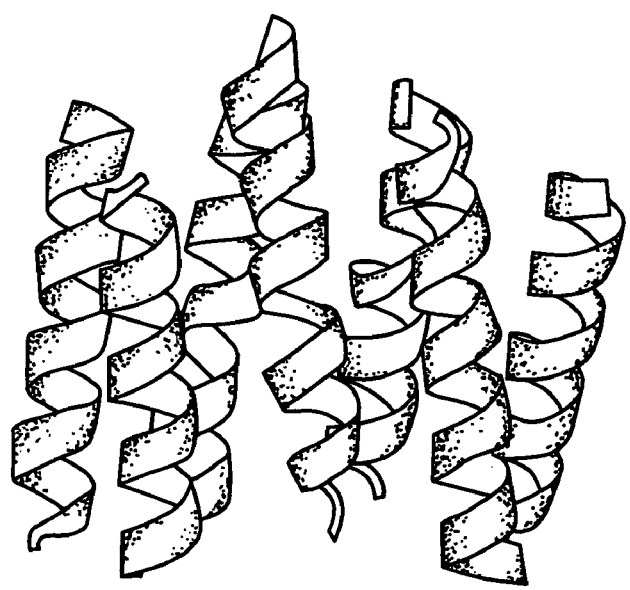
FIG. 2 illustrates the truncated structure of the seven A-chain helices of Bacteriorhodopsin, 1 C3W.

FIG. 2 illustrates the truncated structure of the seven helices of Bacteriorhodopsin after residue elimination. The largest structure, the photosynthetic reaction center, 1JB0, contained thirty-one truncated helices.

The centroid of each residue side-chain of the truncated structure is calculated and the geometric center of the distribution of residue centroids obtained. The shape of a profiling geometry (e.g., sphere, cylinder, cone, ellipsoid, etc.) is then chosen and the hydrophobicity profile is calculated about the axis through the geometric center and normal to the plane of the membrane.

For the structures exhibiting symmetry about the profiling axis, namely 1 C3W, 1 C 17, 1 MSL, and 1 MD, the choice of the profiling geometry was chosen to approximate the overall external shape of the multimer within the lipid bilayer and a series of nested shapes consistent with this geometry were generated. This choice of nested shapes provides contours about the profiling axis that correlate with the lipid exposure for residues proximate to the protein lipid boundary.

For the structures with no symmetry about the profiling axis, an elliptical cylinder was chosen for profiling. At the greatest distances from the profiling axis, averages with ellipses over an irregular distribution of protein centroids will have contributions from local regions that are most distant from the profiling axis. This contrasts with the averages over the symmetric structures where at large distances from the profiling axis, symmetrically related features that are not spatially contiguous are included in the average. Certain consequences of averaging over the structures lacking symmetry are discussed below.

Results are obtained for the Eisenberg and for the GES scales of residue hydrophobicity. The GES scale was chosen since it had been used in the previous calculation alluded to. While these two particular scales have been used, the overall qualitative features described below would be relatively insensitive to the choice of any scale that would similarly segregate the amino acid values of hydrophobicity into a polar, polar uncharged and polar charged residues.

The scales are shifted to provide a value of zero hydrophobicity when all residues of each truncated structure are collected. The shifted values are also scaled to provide a standard deviation of unity for each structure. Since the average value of residue hydrophobicity of the entire structure is then zero, this shift of the scale enables a simple interpretation of the changes in the accumulated values of residue hydrophobicity with increasing distance from the protein interior.

If the value increases with increasing distance from the interior, residues of greater hydrophobic content than the average of the entire structure have been collected. If the value decreases with increasing distance from the interior, residues of lesser hydrophobic content have been collected. Shifting the scale of residue hydrophobicity in this manner provides a baseline for comparison of changes in the spatial distribution of residue hydrophobicity of the truncated structures. It enables concise quantitative statements of the spatial changes in residue hydrophobicity that are independent of the overall hydrophobic content of the structures as well as enabling a comparison of these changes over the spatial extent of different structures.

With the choice of a profiling geometry the values of residue hydrophobicity are then accumulated as a function of increasing size of each nested shape of the profiling geometry until the largest shape encapsulates all of the residues. The accumulated spatial distribution of residue hydrophobicity, or accumulated zero-order moment profile, is given by the function H(d). H(d) is the sum of the values of residue hydophobicity within the circular, elliptical or conical cylinder of radius d.

$$H(d) = \sum_i \frac{h'_i}{d}$$

The $h'_i$ are the shifted and scaled values of hydrophobicity of the ith residue.

The hydrophobicity profile is obtained by calculating the values of H(d) in steps. For example, the steps may be in one or more Angstroms. As previously noted, the changes in H(d) are interpreted simply for each increasing value of d. If H(d) increases, the average hydrophobic value of the residues collected over the shell (e.g., of width one or more Angstroms) is greater than the average value of residue hydrophobicity for the entire structure. If H(d) decreases, residues of lesser than average hydrophobic value have been collected. Any subsequent comment made with regard to increasing or decreasing hydrophobic residue content may then be made with respect to the average value of residue hydrophobicity of the entire structure.

Collecting the values of residue hydrophobicity in this manner provides a set of sequential values of accumulated residue hydrophobicity with increasing distance from the center of the structure to the protein/lipid interface within the bilayer. These values may form a zero-order moment profile of the residue hydrophobicity from the interior to the exterior of the structure.

Such a profile has been previously obtained for thirty soluble globular proteins. However, a second-order moment, which had been used to amplify the distance dependence of the hydrophobicity distribution, and had provided the quasi-invariant hydrophobic-ratio of distances for soluble globular proteins, is not necessarily utilized in the present invention.

FIGS. 3A-D, 4A-D, and 6A-D through 14A-D graphically illustrate the hydrophobicity profiles, H(d), for the structures and the distribution of residue centroids with elliptical or circular boundaries that delimit regions of contrasting behavior. The shapes are mainly inverted with respect to the shapes obtained for the thirty soluble globular proteins previously investigated.

The interior regions exhibit diverse behavior, either populated, on average, by residues of greater than, roughly equal to or of lesser hydrophobic content than the average of the entire structure. All of the profiles display an intermediate spatial region of decreasing hydrophobic content. At the most distant values from the interior, the majority of the profiles increase, on average, with increasing distance. The few profiles that do not, namely, profiles of the structures 1KF6, 1 BE3, and 1JB0, reflect averages over local regions of the interface and not averages over a major portion of the interface. The average over the major fraction of the interface near the protein-lipid boundary shows a statistical increase in residue hydrophobic content with decreasing distance to the protein-lipid interface for all eleven structures.

Figure 3A:
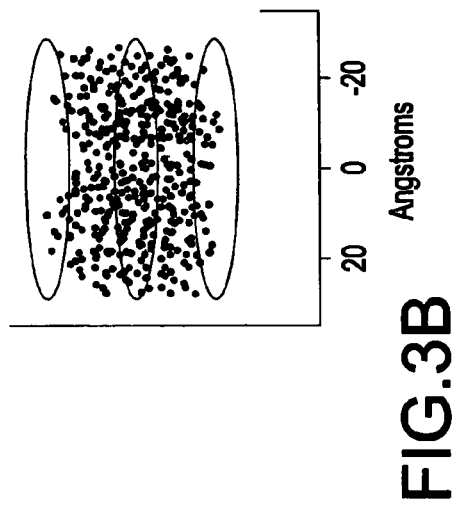
FIGS. 3A-3D illustrate a distribution of residue centroids and hydophobicity profiles of Bacteriorhodopsin, 1C3W, according to an exemplary embodiment of the present invention.
Figure 3B:
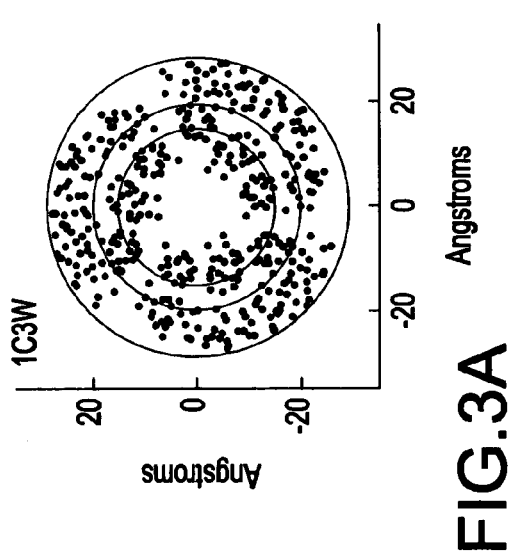
Figure 3C:
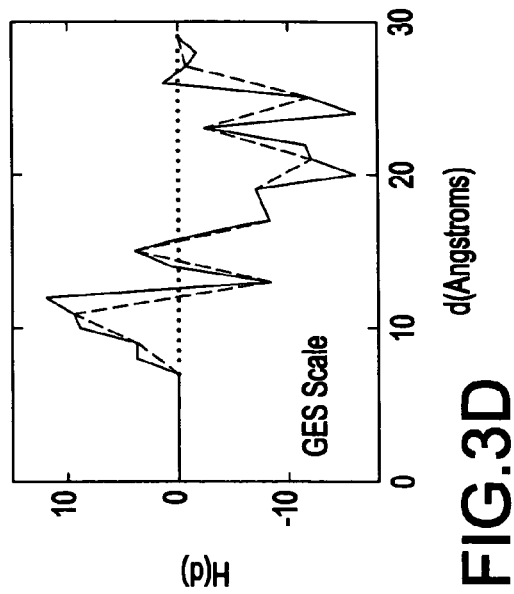
Figure 3D:
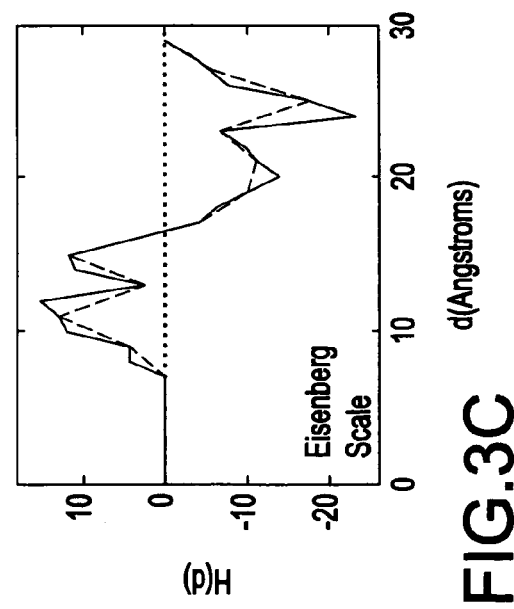

FIGS. 3A-3D illustrate a distribution of residue centroids and hydophobicity profiles of Bacteriorhodopsin, 1C3W. FIG. 3A illustrates a view of along the C3 symmetry axis normal to the plane of the membrane. FIG. 3B illustrates a view canted by 80 degrees from the symmetry axis. FIG. 3C illustrates the hydrophobicity profile, H(d), calculated with the Eisenberg hydrophobicity scale. FIG. 3D illustrates the hydrophobicity profile, H(d), calculated with the GES hydrophobicity scale. The solid and dashed lines in FIGS. 3C and 3D are calculated in steps of one and two Angstroms, respectively;

Profile features will be related to the structural features of the α-helical bundles for the structures exhibiting symmetry. Bacteriorhodopsin (1 C3W) has been profiled with a series of nested cylinders of varying radii. FIG. 3A is a view along the C3 symmetry axis that lies close to the perpendicular to the plane of the membrane. The distribution of residue centroids is shown along with three cylindrical circular crosssections of different radii. The largest cylinder with a radius of 29 Angstroms encloses all residue centroids. FIG. 3B is a view that is canted by 80 degrees from this axis. Three circular cross sections of the largest cylinder are shown in FIG. 3B.

FIGS. 3C and 3D show H(d) calculated with the Eisenberg and the GES residue hydrophobicity scales, respectively. The general trends with increasing radial distance from the cylindrical axis are similar. The first six hydrophobic residues are collected at eight Angstroms. There is a subsequent increase in H(d), indicating the collection of residues of increasing hydrophobic content within the protein interior.

In the range of 15 to 20 Angstroms, the accumulation of hydrophilic residues and diminishing accumulation of hydrophobic residues is responsible for the plunge to negative values. This range of distances spans the range between the two inner circles of FIG. 3A, which delineate the region between the inner and outer nested bundles of α-helices. In this region are the water bound molecules, the retinal Schiff bases, and three arginine, lysine, and aspartic acid residues. From 24 Angstroms to final residue accumulation at 29 Angstroms there is an increase in the numbers hydrophobic residues collected which includes thirty leucine and valine residues.

Figure 4A:
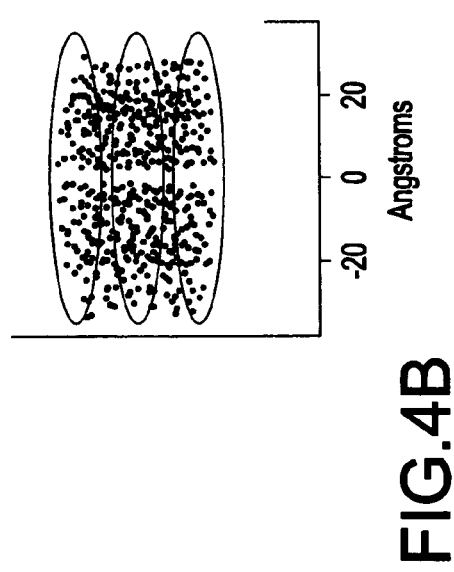
FIGS. 4A-4D illustrate a distribution of residue centroids and hydrophobicity profiles of the subunit C of the ATP synthase from *Escherichia coli*, 1 C 17, according to an exemplary embodiment of the present invention.
Figure 4B:
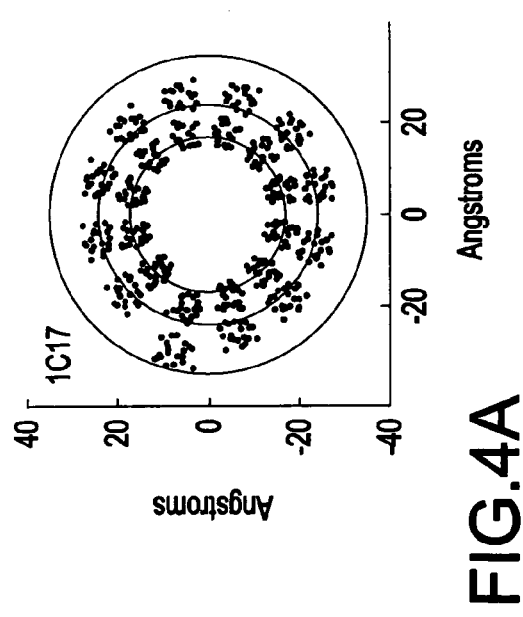
Figure 4C:
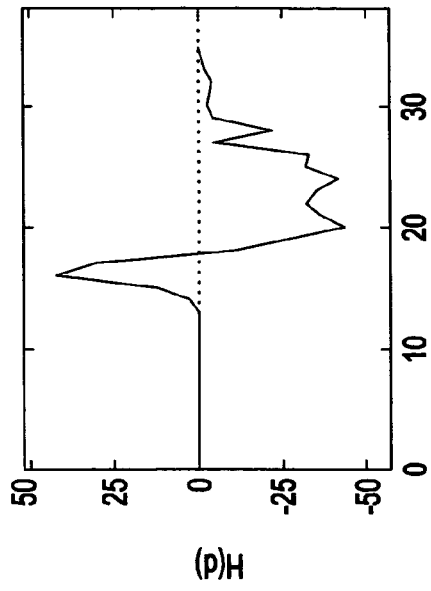
Figure 4D:
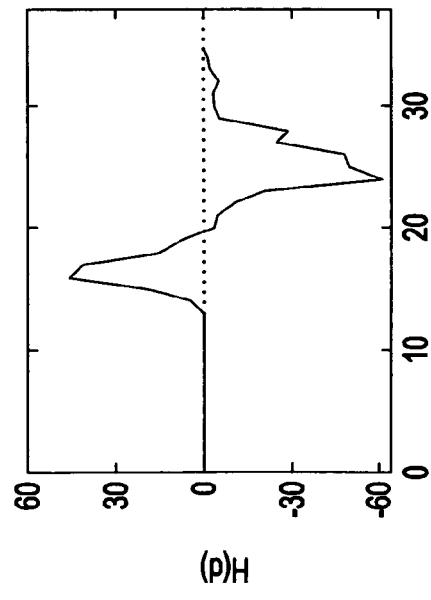

FIGS. 4A-4D illustrate a distribution of residue centroids and hydrophobicity profiles of the subunit C of the ATP synthase from *Escherichia coli*, 1 C 17. FIG. 4A illustrates a view of along the C3 symmetry axis normal to the plane of the membrane. FIG. 4B illustrates a view canted by 80 degrees from the symmetry axis. FIG. 4C illustrates the hydrophobicity profile, H(d), calculated with the Eisenberg hydrophobicity scale. FIG. 4D illustrates the hydrophobicity profile, H(d), calculated with the GES hydrophobicity scale. The solid lines in FIGS. 4C and 4D are calculated in steps of one Angstroms.

Specifically, FIG. 4A shows the truncated residue centroid distribution of 1 C 17 with a view along the normal to the plane of the membrane. The truncated helices of all twelve chains are approximately perpendicular to the plane of the membrane. The slight deviation from cylindrical symmetry is partially accounted for by the presence of the M chain. This chain which is adjacent to the helical bundle with approximate cylindrical symmetry, has been deleted in the present calculation.

Since the truncated structure exhibits approximate cylindrical symmetry, profiling was performed with a cylinder of elliptical cross section. The largest ellipse shown in FIG. 4A, enclosing all residue centroids, has a major principal axis of 35 Angstroms. The hydrophobicity profiles, FIGS. 4C and 4D, have shapes qualitatively similar to Bacteriorhodopsin. The profiles show an initial increase in hydrophobicity after collection of the first three residues at 14 Angstroms.

Between the range of values from 17 to 24 Angstroms, there is a significant reduction in the hydrophobic content of the residues collected. This is the range of distances between the two inner ellipses of FIG. 4A, and is the range of distances between the inner and outer sets of nested helices. The final region of residue accumulation, between the values of 24 and 35 Angstroms, displays an increase in hydrophobic residue content as the protein-lipid interface from within the bilayer is approached.

Of the eleven, 1 C3W and 1 C 17 are the only structures with approximate cylindrical symmetry and with helical axes lying near the normal to the lipid bilayer. Profiles about the cylindrical axes with such orientation will reflect the demarcation between α-helical nested structures differently from helices that are canted with respect to the bilayer surface. Based on these profiles, it may be surmised that a region of decreasing hydrophobic content may be a general feature of the residue distribution between the nested α-helical bundles of transmembrane proteins.

Figure 5:
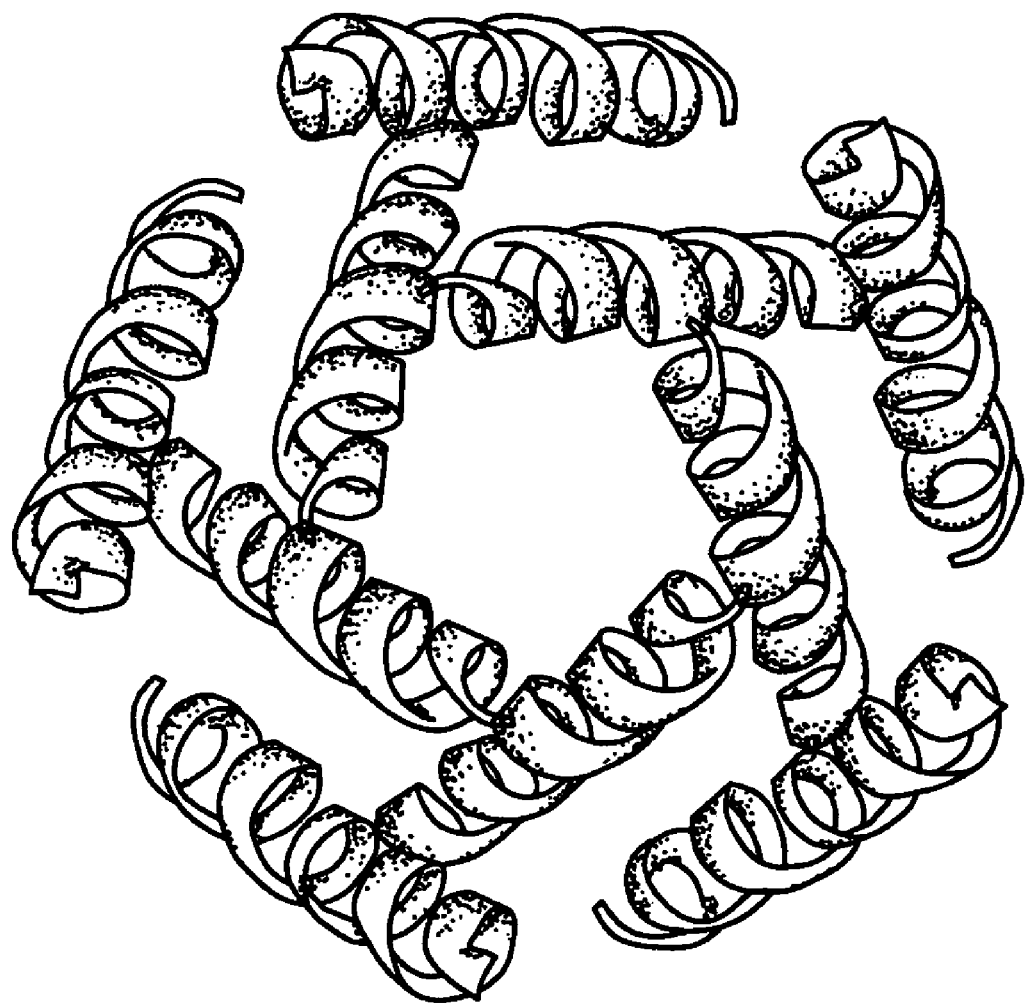
FIG. 5 illustrates a view, along the normal to the membrane surface, of the helices of the truncated multimer of the mechanosensitive ion channel, 1 MSL.

FIG. 5 is a view of the helices of the truncated mechanosensitive ion channel, 1MSL, along the normal to the membrane surface. Like Bacteriorhodopsin there are sets of interior and exterior helices, which are canted, however, with respect to the membrane surface.

Figure 6A:
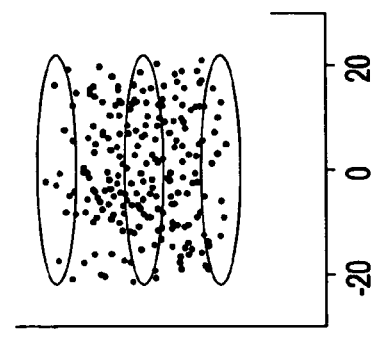
FIGS. 6A-6D illustrate a distribution of residue centroids and hydrophobicity profiles of the gated mechanosensitive ion channel from *Mycobacterium tuberculosis*, 1MSL, according to an exemplary embodiment of the present invention.
Figure 6B:
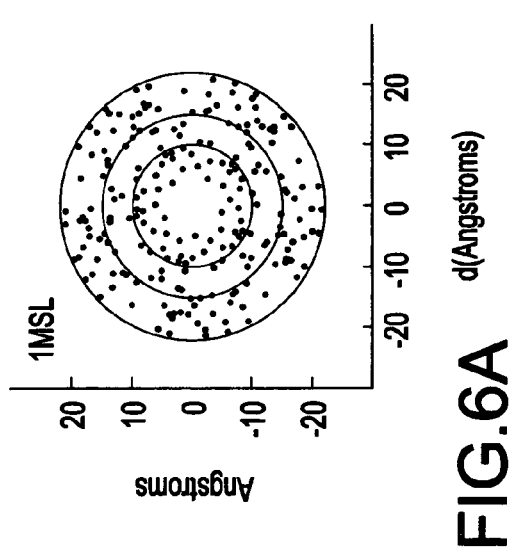
Figure 6C:
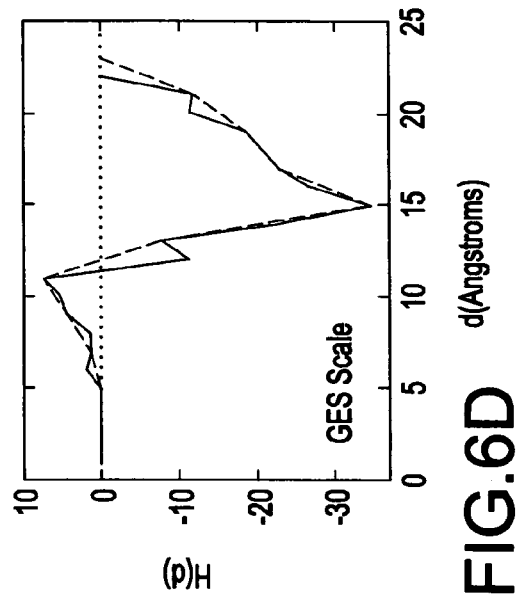
Figure 6D:
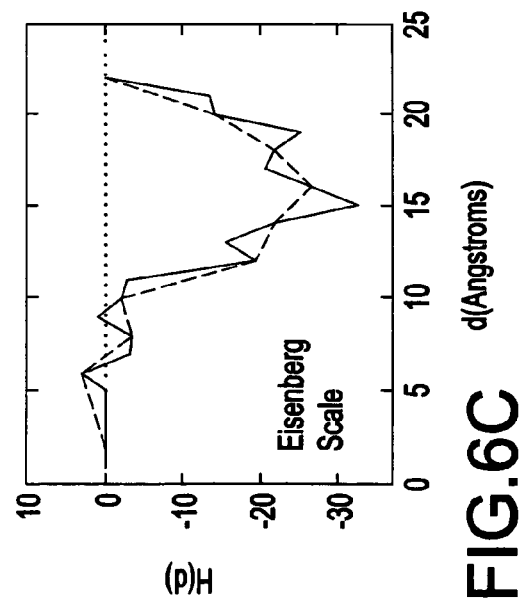

FIGS. 6A-6D illustrate a distribution of residue centroids and hydophobicity profiles of the gated mechanosensitive ion channel from *Mycobacterium tuberculosis*, 1MSL. FIG. 6A illustrates a view of along the C3 symmetry axis normal to the plane of the membrane. FIG. 6B illustrates a view canted by 80 degrees from the symmetry aids. FIG. 6C illustrates the hydrophobicity profile, H(d), calculated with the Eisenberg hydrophobicity scale. FIG. 6D illustrates the hydrophobicity profile, H(d), calculated with the GES hydrophobicity scale. The solid and dashed lines in FIGS. 6C and 6D are calculated in steps of one and two Angstroms, respectively.

A view, along the normal to the surface of the bilayer, of the distribution of residue centroids, FIG. 6A, reveals a region of separation between the centroids of the interior and exterior helices. This region, from ten to fifteen Angstroms is between the two inner circles shown in FIG. 6A. FIGS. 6C and 6D show a decrease in residue hydrophobic content with increasing distance within this region, which is similar to that observed for 1 C3W and 1 C 17.

The prominent increase in hydrophobic content over the range of interior distances is, however, not observed. With increasing radial distance in the region of the multimer proximate to the proteinlipid interface, one observes increasing residue hydrophobic content. Since the truncated transmembrane protein structure of the potassium ion channel, 1 K4D, has an overall conical shape, a cone has been chosen as the profiling geometry. The pitch of the cone is chosen visually to register closely with the exterior distribution of residue centroid locations. As has been mentioned, the nested conical contours will correlate with lipid exposure for residues that are near the protein-lipid boundary.

Figure 7A:
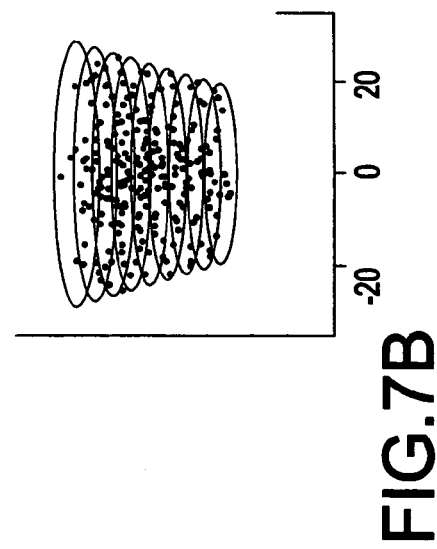
FIGS. 7A-7D illustrate a distribution of residue centroids and hydrophobicity profiles of the potassium ion channel from *Streptomyces lividans*, 1K4D, according to an exemplary embodiment of the present invention.
Figure 7B:
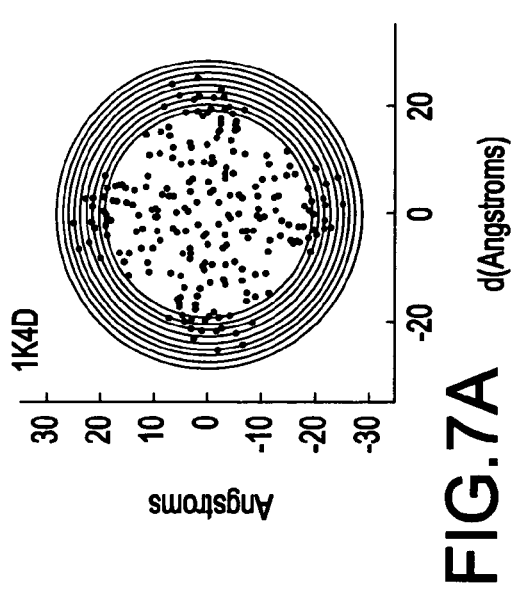
Figure 7C:
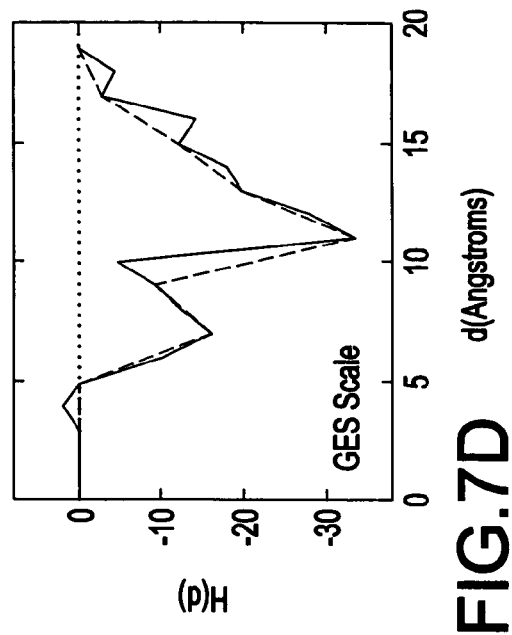
Figure 7D:
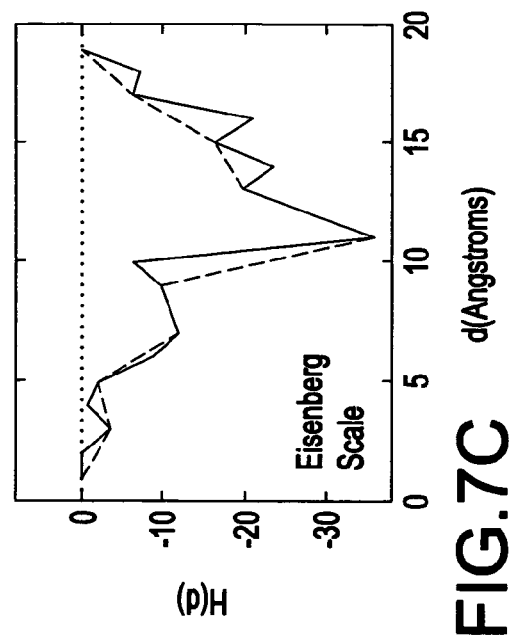

FIGS. 7A-7D illustrate a distribution of residue centroids and hydophobicity profiles of the potassium ion channel from *Streptomyces lividans*, 1K4D. FIG. 7A illustrates a view of along the symmetry axis normal to the plane of the membrane. FIG. 7B illustrates a view canted by 80 degrees from the symmetry axis. FIG. 7C illustrates the hydrophobicity profile, H (d), calculated with the Eisenberg hydrophobicity scale. FIG. 7D illustrates the hydrophobicity profile, H(d), calculated with the GES hydrophobicity scale. The solid and dashed lines in FIGS. 7C and 7D are calculated in steps of one and two Angstroms, respectively. d is the radius of the smallest radial cross section of the cone.

The protein has fourfold symmetry about the normal to the membrane surface and the cone is created with varying spherical cross sections along the conical axis. FIG. 7B is a view of the distribution of centroids along a direction tilted by 80 degrees from the normal to the membrane surface. The circles of varying radii delineate the cone just large enough to enclose all of the residue centroids. FIG. 7A is a view along the normal to the membrane surface. The set of circular cross sections shown, differs from previous sets shown since cross sections for only one profiling conical geometry have been displayed. The different circles delineate the different conical cross-sections of the cone that just enclose all of the centroids.

FIGS. 7C and 7D show the accumulated hydrophobicity, H(d), as a function of the radius, d. d is the radius of the smallest circular cross section of each of the cones of the nested set of conical structures. The significant drop in hydrophobic content between 10 and 11 angstroms is due to the collection of four Arginine residues. Both residue hydrophobicity scales yield an inverted profile with respect to that found for the thirty globular soluble proteins. This again indicates that residues nearer to the protein-lipid interface have increased hydrophobic character with respect to the interior residues.

As the profiling geometry increases in extent over the structures lacking symmetry, it sweeps out spatial regions within nested ellipsoids that bear little or no structural resemblance to each other. Consequently, a detailed description of the correspondence between profile features and structural features would be extensive and will not be provided. Profiles of these structures, FIGS. 8A-D through FIGS. 14A-D, are mainly inverted with respect to that found for the soluble proteins.

Figure 8B:
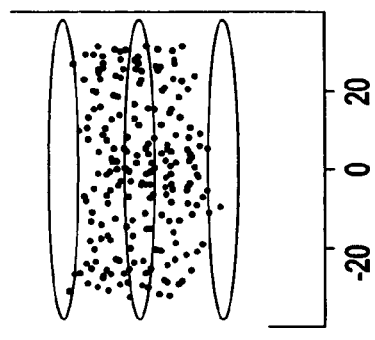
FIG. 8A-8D illustrate a distribution of residue centroids and hydrophobicity profiles of the photosynthetic reaction center, *Rhodobacter sphaeroides*, 1PCR, according to an exemplary embodiment of the present invention.
Figure 8A:
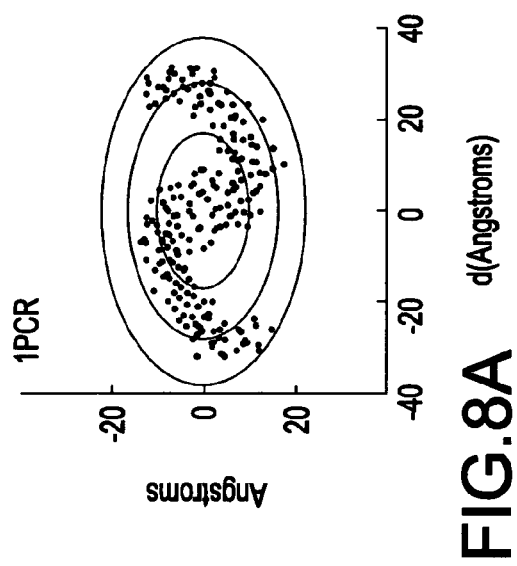
Figure 8D:
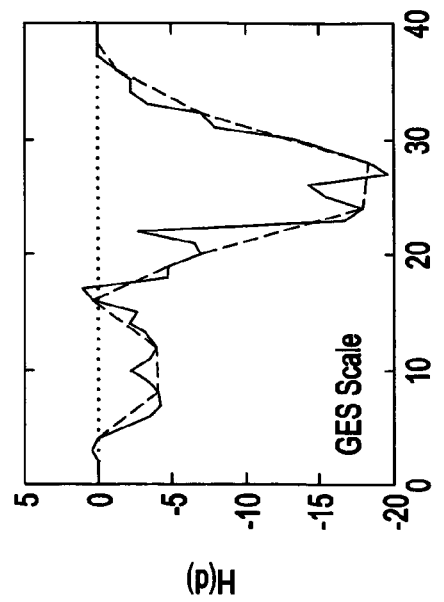
Figure 8C:
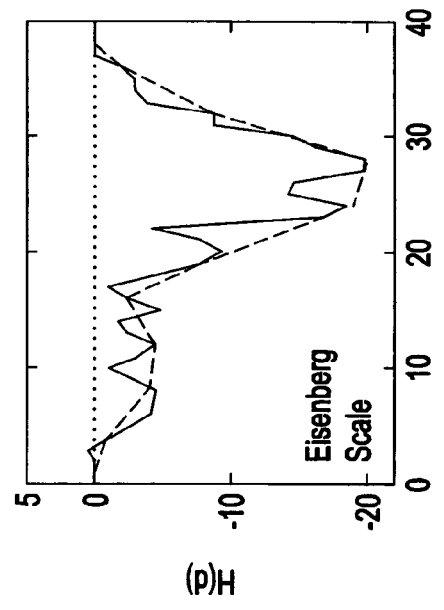

FIGS. 8A-8D illustrate a distribution of residue centroids and hydrophobicity profiles of the photosynthetic reaction center, *Rhodobacter sphaeroides*, 1PCR. FIG. 8A illustrates a view along the axis normal to the plane of the membrane. FIG. 8B illustrates a view canted by 80 degrees from the symmetry axis. FIG. 8C illustrates the hydrophobicity profile, H(d), calculated with the Eisenberg hydrophobicity scale. FIG. 8D illustrates the hydrophobicity profile, H(d), calculated with the GES hydrophobicity scale. The solid and dashed lines in FIGS. 8C and 8D are calculated in steps of one and four Angstroms, respectively.

Figure 9A:
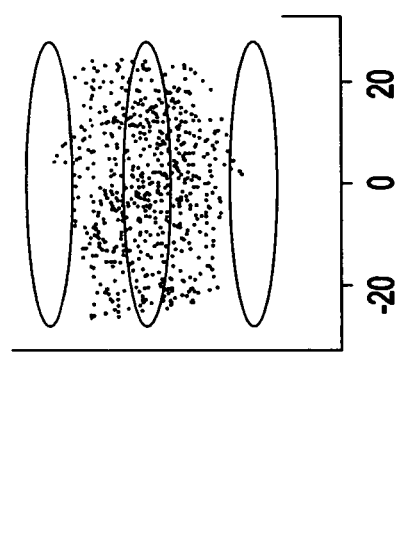
FIGS. 9A-9D illustrate a distribution of residue centroids and hydophobicity profiles of the Cytochrome-C Oxidase, 1EHK, according to an exemplary embodiment of the present invention.
Figure 9B:
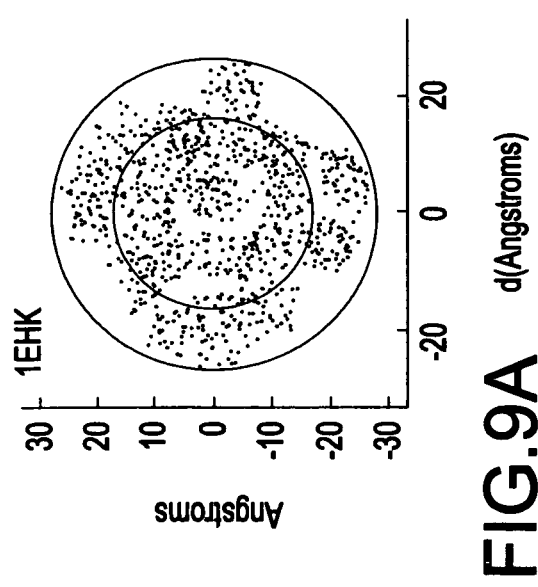
Figure 9C:
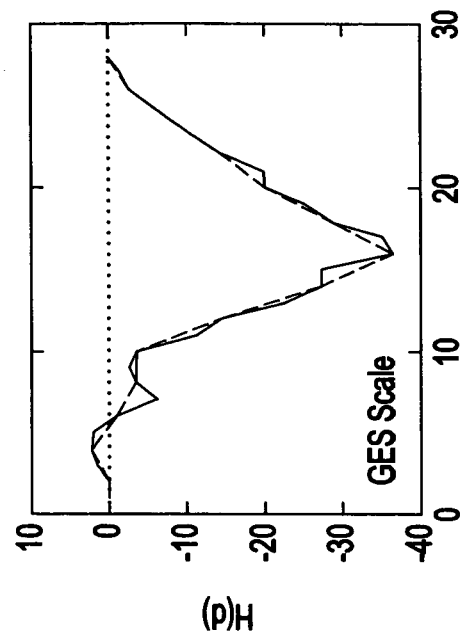
Figure 9D:
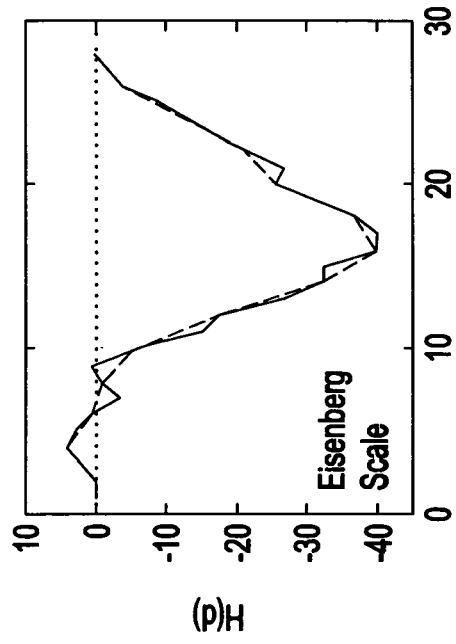

FIGS. 9A-9D illustrate a distribution of residue centroids and hydophobicity profiles of the Cytochrome-C Oxidase, 1EHK. FIG. 9A illustrates a view along the axis normal to the plane of the membrane. FIG. 9B illustrates a view canted by 80 degrees from the symmetry axis. FIG. 9C illustrates the hydrophobicity profile, H(d), calculated with the Eisenberg hydrophobicity scale. FIG. 9D illustrates the hydrophobicity profile, H(d), calculated with the GES hydrophobicity scale. The solid and dashed lines in FIGS. 9C and 9D are calculated in steps of one and two Angstroms, respectively.

FIGS. 10A-10D illustrate a distribution of residue centroids and hydophobicity profiles of the Aqpl Water Channel, 1J4N. FIG. 10A illustrates a view along the axis normal to the plane of the membrane. FIG. 10B illustrates a view canted by 80 degrees from the symmetry axis. FIG. 10C illustrates the hydrophobicity profile, H(d), calculated with the Eisenberg hydrophobicity scale. FIG. 10D illustrates the hydrophobicity profile, H(d), calculated with the GES hydrophobicity scale. The solid and dashed lines in FIGS. 10C and 10D are calculated in steps of one and two Angstroms, respectively.

Figure 11A:
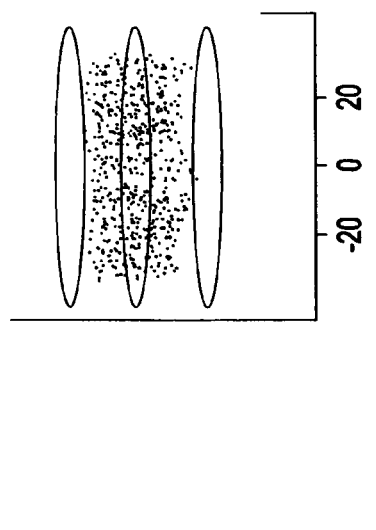
FIGS. 11A-11D illustrate a distribution of residue centroids and hydophobicity profiles of the Bacterial Abc Transporter, 1L7V, according to an exemplary embodiment of the present invention.
Figure 11B:
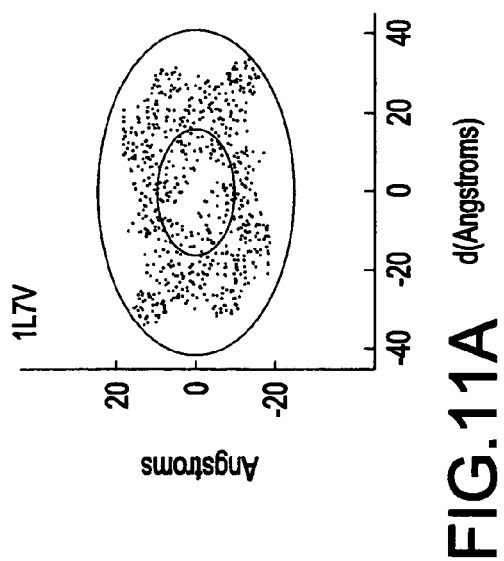
Figure 11C:
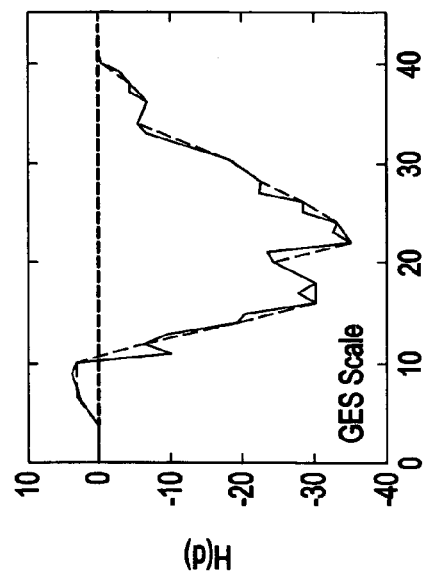
Figure 11D:
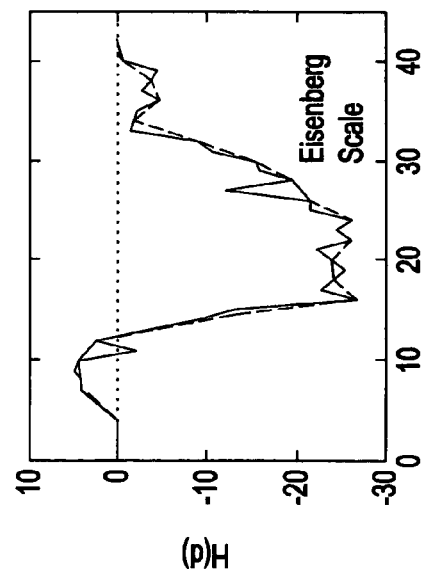

FIGS. 11A-11D illustrate a distribution of residue centroids and hydophobicity profiles of the Bacterial Abc Transporter, 1L7V. FIG. 11A illustrates a view along the axis normal to the plane of the membrane. FIG. 11B illustrates a view canted by 80 degrees from the symmetry axis. FIG. 11C illustrates the hydrophobicity profile, H (d), calculated with the Eisenberg hydrophobicity scale. FIG. 11D illustrates the hydrophobicity profile, H(d), calculated with the GES hydrophobicity scale. The solid and dashed lines in FIGS. 11C and 11D are calculated in steps of one and two Angstroms, respectively.

Figure 12A:
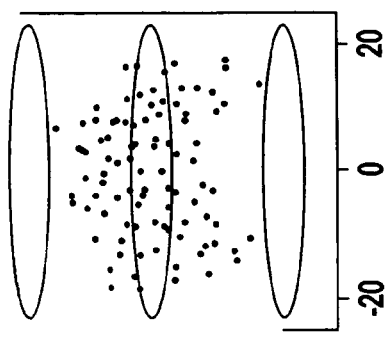
FIGS. 12A-12D illustrate a distribution of residue centroids and hydophobicity profiles of *E. Coli* Quinol-Fumarate Reductase, 1KF6, according to an exemplary embodiment of the present invention.
Figure 12B:
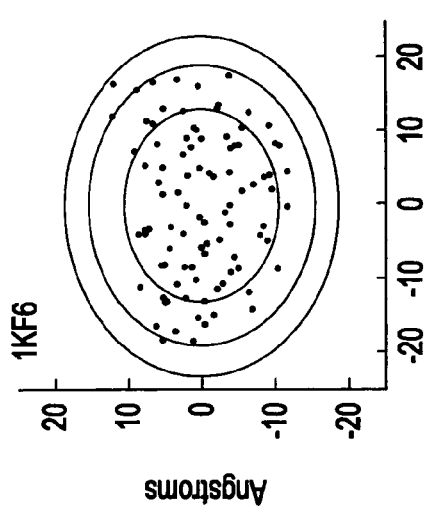
Figure 12C:
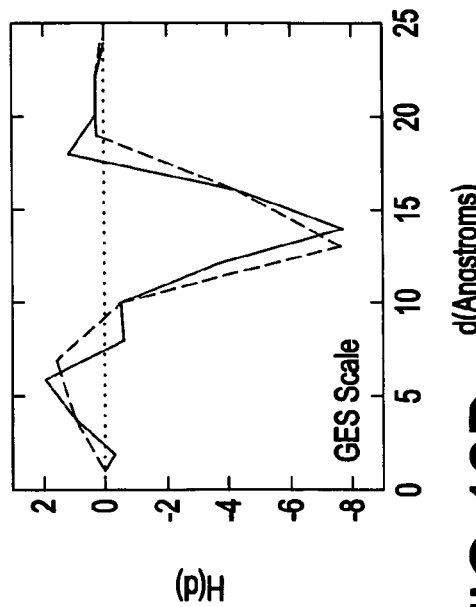
Figure 12D:
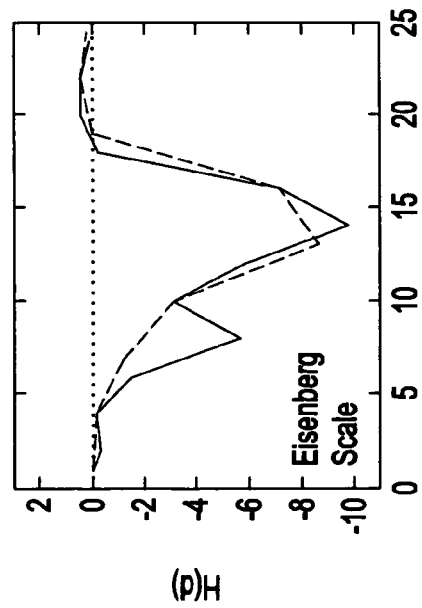

FIGS. 12A-12D illustrate a distribution of residue centroids and hydophobicity profiles of *E. Coli* Quinol-Fumarate Reductase, 1KF6. FIG. 12A illustrates a view along the axis normal to the plane of the membrane. FIG. 12B illustrates a view canted by 80 degrees from the symmetry axis. FIG. 12C illustrates the hydrophabicity profile, H(d), calculated with the Eisenberg hydrophobicity scale. FIG. 12D illustrates the hydrophobicity profile, H(d), calculated with the GES hydrophobicity scale. The solid and dashed lines in FIGS. 12C and 12D are calculated in steps of two and three Angstroms, respectively.

Figure 13B:
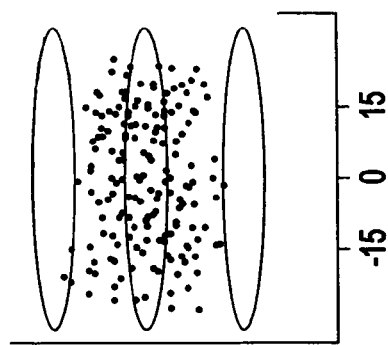
FIGS. 13A-13D illustrates a distribution of residue centroids and hydophobicity profiles of the Cytochrome Bc 1 Complex, 1 BE3, according to an exemplary embodiment of the present invention.
Figure 13D:
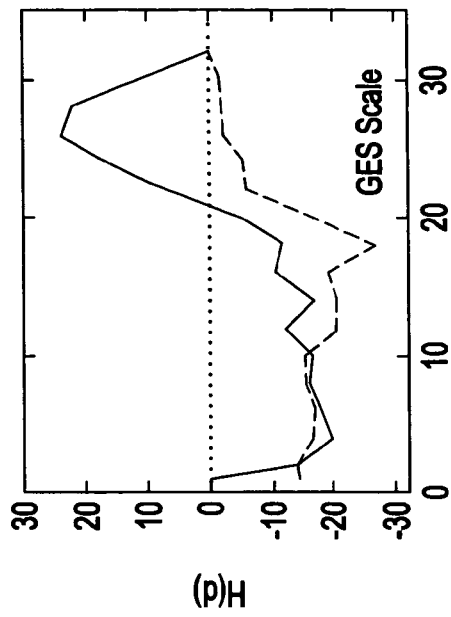
Figure 13A:
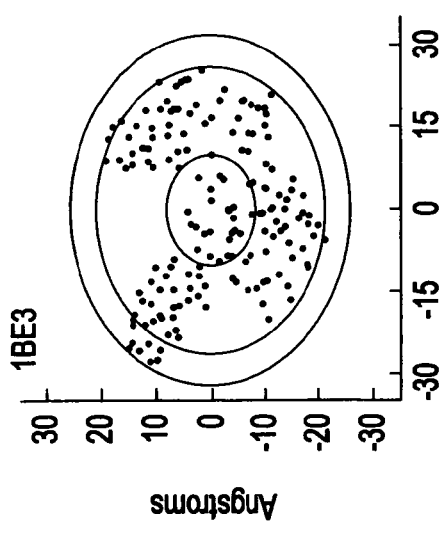
Figure 13C:
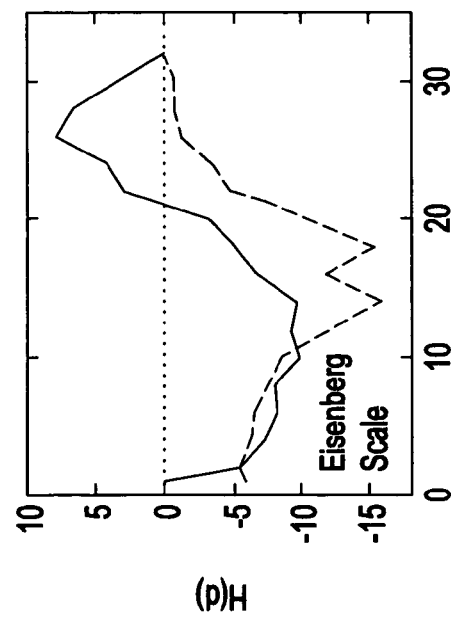

FIGS. 13A-13D illustrates a distribution of residue centroids and hydrophobicity profiles of the Cytochrome Bc 1 Complex, 1 BE3. FIG. 13A illustrates a view along the axis normal to the plane of the membrane. FIG. 13B illustrates a view canted by 80 degrees from the symmetry axis. FIG. 13C illustrates the hydrophobicity profile, H(d), calculated with the Eisenberg hydrophobicity scale. FIG. 13D illustrates the hydrophobicity profile, H(d), calculated with the GES hydrophobicity scale. Both solid and dashed lines in FIGS. 13C and 13D are calculated in steps of two Angstroms. The solid line is calculated with the inclusion of the D helical chain. The dashed line is calculated with deletion of this chain.

Figure 14B:
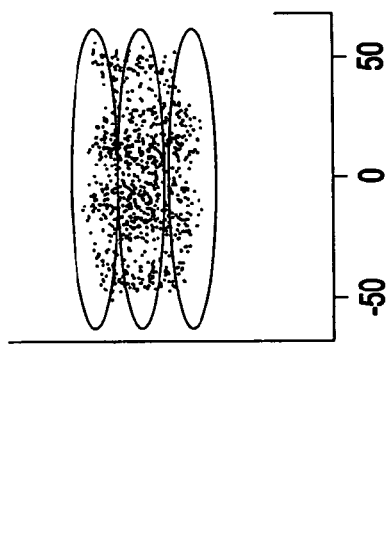
FIGS. 14A-14D illustrate a distribution of residue centroids and hydophobicity profiles of the Photosynthetic Reaction Center: Photosystem I, 1JB0, according to an exemplary embodiment of the present invention.
Figure 14A:
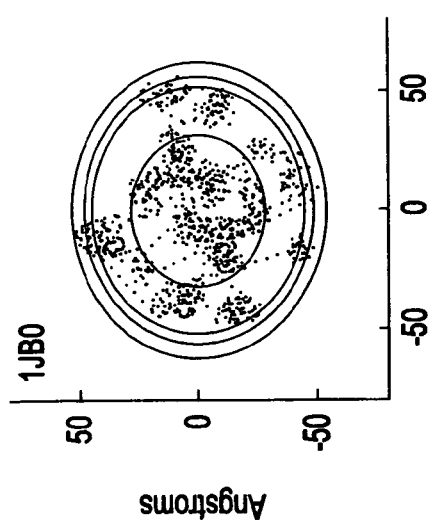
Figure 14D:
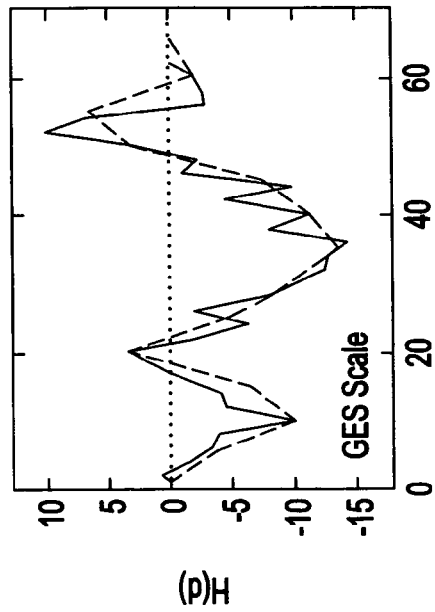
Figure 14C:
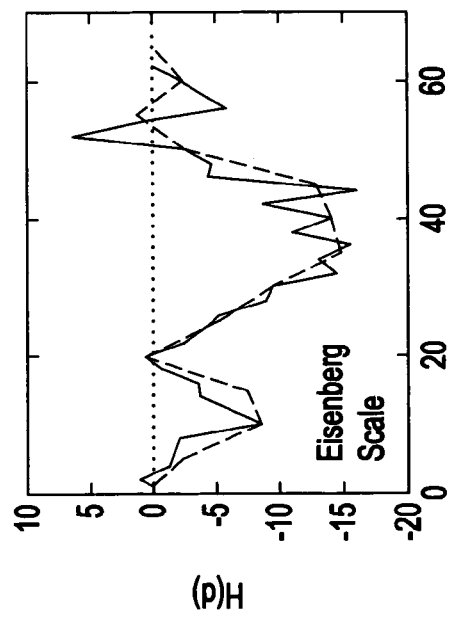

FIGS. 14A-14D illustrate a distribution of residue centroids and hydrophobicity profiles of the Photosynthetic Reaction Center: Photosystem I, 1JB0. FIG. 14A illustrates a view along the axis normal to the plane of the membrane. FIG. 14B illustrates a view canted by 80 degrees from the symmetry axis. FIG. 14C illustrates the hydrophobicity profile, H(d), calculated with the Eisenberg hydrophobicity scale. FIG. 14D illustrates the hydrophobicity profile, H(d), calculated with the GES hydrophobicity scale. The solid and dashed lines in FIGS. 14C and 14D are calculated in steps of two and five Angstroms, respectively.

It should be noted that of these structures (e.g., FIGS. 8A-D through 14A-D), three show little change or a decrease in hydrophobic content at the farthest distances from the interior. These are the structures, 1K6, 1BE3, and 1JB0, FIGS. 12A-D through 14A-D. These particular profile features are not representative of residue accumulation along the major fraction of the periphery of the protein-lipid interface.

The truncated helical bundle, 1 KF6, in the range of 19 angstroms to complete residue collection at 23 angstroms (e.g., see FIG. 12A) collects only few residues at two different spatial locations. These residues have, on average, a hydrophobic content comparable to the average hydrophobicity of the entire multimer. The residues collected in the range of values from 15 to 19 angstroms are greater in number and span the major fraction of the protein-lipid interface. Over this range of distances the hydrophobic residue content, on average, increases as the interface is approached.

The profiles of the 1BE3 multimer, the solid lines in FIGS. 13C and 13D, show a decrease in hydrophobic content over a range of distances, 26 Angstroms to complete residue collection at 32 Angstroms. This behavior is a consequence of the residues of the helical D chain having an average value of hydrophobicity that is less than that of the entire multimer. Profiling the structure with deletion of the D chain yields the dashed profiles shown in FIGS. 13C and 13D. The major fraction of the periphery of the multimer then shows increasing hydrophobic content as the interface with the lipid is approached.

The profiles, FIGS. 14C and 14D, of the multimer, 1JB0, the most structurally complex structure examined, with multiple chains, show a narrow range of decreasing hydrophobic content with distance close to the lipid interface. This range of distances is illustrated in FIG. 14A. It is the narrow range of distances between the two closest ellipses. Averages over this range of distances arise from accumulation over several different local regions near the interface.

The decrease in hydrophobic content at a distance of 56 Angstroms is due to the collection of one arginine and one lysine residue in different local regions. Both residues are not only near the protein-lipid interface within the bilayer but in the vicinity of the bilayer surface as well. From 56 Angstroms to final residue collection at 62 Angstroms there is an increase in hydrophobic content. Differences in the profiles in this narrow spatial region dependent upon windowing size and the choice of the hydrophobicity scale should also be noted.

The profiles of 1BE3 and 1JB0 emphasize that the distribution of residue hydrophobicity exhibits variations not only in an "inside-outside" or radial direction but in an angular direction as well, near to and along the periphery of the protein-lipid interface. Such variations can be investigated by profiling along the protein-lipid periphery.

As has been seen, local regions in the vicinity of the protein-lipid interface may be of lesser hydrophobic content than the multimeric average. It is of interest that so few such variations have been seen in the eleven structures examined. Finally, when profiling a complex structure with multiple helical chains, the baseline for comparison is important, e.g., which of the chains are to be chosen to provide the reference value of hydrophobicty against which local variations are to be compared.

A statistical advantage of collecting the values of residue hydrophobicity within a profiling surface that increases in size involves a reduction in the fluctuations about the mean, compared with collecting the values of residue hydrophobicity within each shell bounded by adjacent nested profiling surfaces. The total residue hydrophobicity within each shell divided by the numbers of residues in the shell, calculated with increasing distance from the axial center of the profiling geometry, provides the residue hydrophobicity density, $\rho(d)$, as a function of distance, d, from the center of the structure.

Despite the fluctuations in value, this density is of interest. This density is illustrated, for example, in FIGS. 15A-F for the four symmetric $\alpha$-helical transmembrane bundles, over the larger half of the radial distances, d, from the cylindrical axis; the range of distances nearer the protein lipid interface. The solid lines are the results of calculations for shells of one Angstrom in thickness. The dashed lines are for shells of two Angstroms thickness. It should be noted that on average, despite the fluctuations in value, the density of the four transmembrane structures exhibits increasing hydrophobic content as the protein lipid interface is approached.

FIGS. 15E and 15F, pertaining to the soluble proteins, 1AKZ and 3PBG, have been included to highlight the different behavior of these proteins. For these proteins, the hydrophobic content decreases as the protein lipid interface is approached. These results obtained for 1AKZ and 3PBG are typical of the thirty soluble proteins previously profiled.

As noted from the FIGS. 15A-15F, however, the spatial decrease in the hydrophobic densities of the soluble proteins, 1AKZ and 3PBG, is more pronounced than the increase observed for the transmembrane structures. Comparing peak height amplitudes of the accumulated profiles of the soluble proteins with the amplitudes of the peak valleys of the $\alpha$-helical structures generally highlights this more modest segregation of the residue hydrophobic content of the transmembrane bundles.

The terminology, "inside-out", had been used previously in connection with a comparison between the spatial hydrophobicity distributions of transmembrane and soluble globular proteins. For the Eisenberg hydrophobicity scale, which is a consensus set of values that approximates the free energy of transfer of the side chain of the amino acid from water to an a polar environment, the average value per residue of thirty soluble globular proteins is −0.13 kcal/mole.

Further, the average value per residue of the four symmetric transmembrane bundles is 0.27 kcal/mole. The difference between these two values is comparable to the difference between the values of Threonine and Alanine on this scale.

The inventor further calculated the differences about the mean value of hydrophobicity for each of the structures. This requires a redistribution of the individual values of residue hydrophobicity for each structure, a result achieved by scaling the values of residue hydrophobicity such that the net hydrophobicity of each structure vanished.

FIG. 16 provides Table 1 which lists the shifted and normalized values of amino acid hydrophobicity that had provided the values of the densities, $\rho(d)$. It should be noted that a significant difference exists between the values for the soluble and transmembrane structures, as well as a range of values of opposite sign, within the lines drawn. These are the values that yield what might be called an "inside-out" distribution of the hydrophobic density of the four symmetric transmembrane bundles relative to the soluble proteins, 1AKZ and 3PBG. These values are a measure of differences about averages, with averages that are very different. The distributions are not "inside-out" in the traditional sense in which each residue is considered to have a fixed polar or a polar identity.

In short, the present invention may be used to examine the spatial distribution of transmembrane residue hydrophobicity from a perspective that is different from the point of view of conventional calculations. The spatial profile may be obtained directly, without reference to solvent-lipid exposure. This provides a view of the variation of residue hydrophobicity from the interior to the exterior of the α-helical bundles buried within the surrounding lipid.

Further, the scaling the residue hydrophobicity for each multimer enables variations about the mean value of hydrophobicity over the spatial extent of the structure to be simply identified. This also enables a comparison of the profiles over the spatial extent of different structures with average values of hydrophobicity that are different. Such a procedure had previously identified comparable length scale features of the profiles of thirty soluble globular proteins of arbitrary structure and size.

The profiles of the α-helical buried bundles, while exhibiting certain differences, exhibit a comparable length scale feature as well. This is the onset of the decrease in hydrophobic residue content at distances from the interior that are at roughly half the spatial extent of the bundle. Consequently, the profiles are mainly inverted with respect to the profiles of the soluble globular proteins. The region proximate to the protein-lipid interface, that had generated previous contention, generally exhibits the increase in average residue hydrophobic content identified by previous calculations. The profiling of the structures lacking symmetry show that such increase need not occur in every local region proximate to the protein-lipid periphery.

Figure 17:
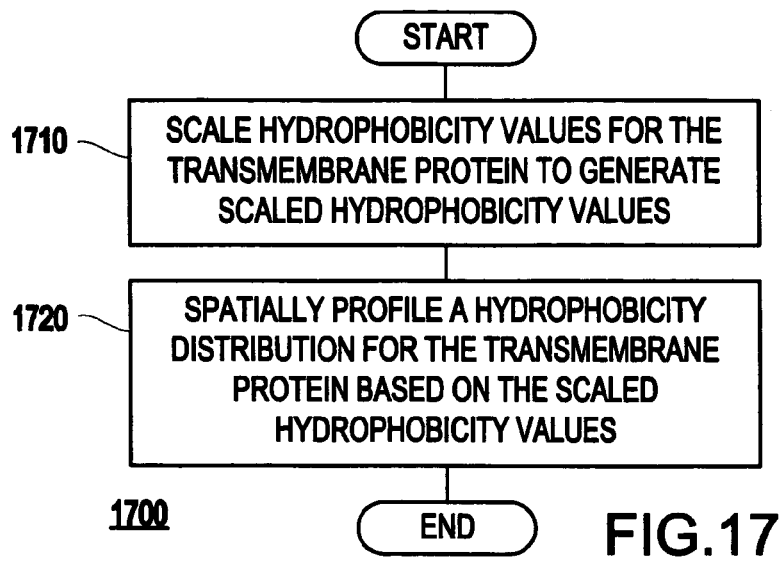
FIG. 17 is a flowchart illustrating a method of spatially profiling a hydrophobicity distribution for a transmembrane protein, according to an exemplary embodiment of the present invention.

Referring again to the drawings, FIG. 17 illustrates a method 1700 of spatially profiling a hydrophobicity distribution for a transmembrane protein. The method 1700 includes scaling hydrophobicity values (1710) for the transmembrane protein to generate scaled hydrophobicity values, and spatially profiling (1720) a hydrophobicity distribution for the transmembrane protein based on the scaled hydrophobicity values. Specifically, the method 1700 may be performed in a manner which is similar to that outlined above with respect to the system 100.

Figure 18:
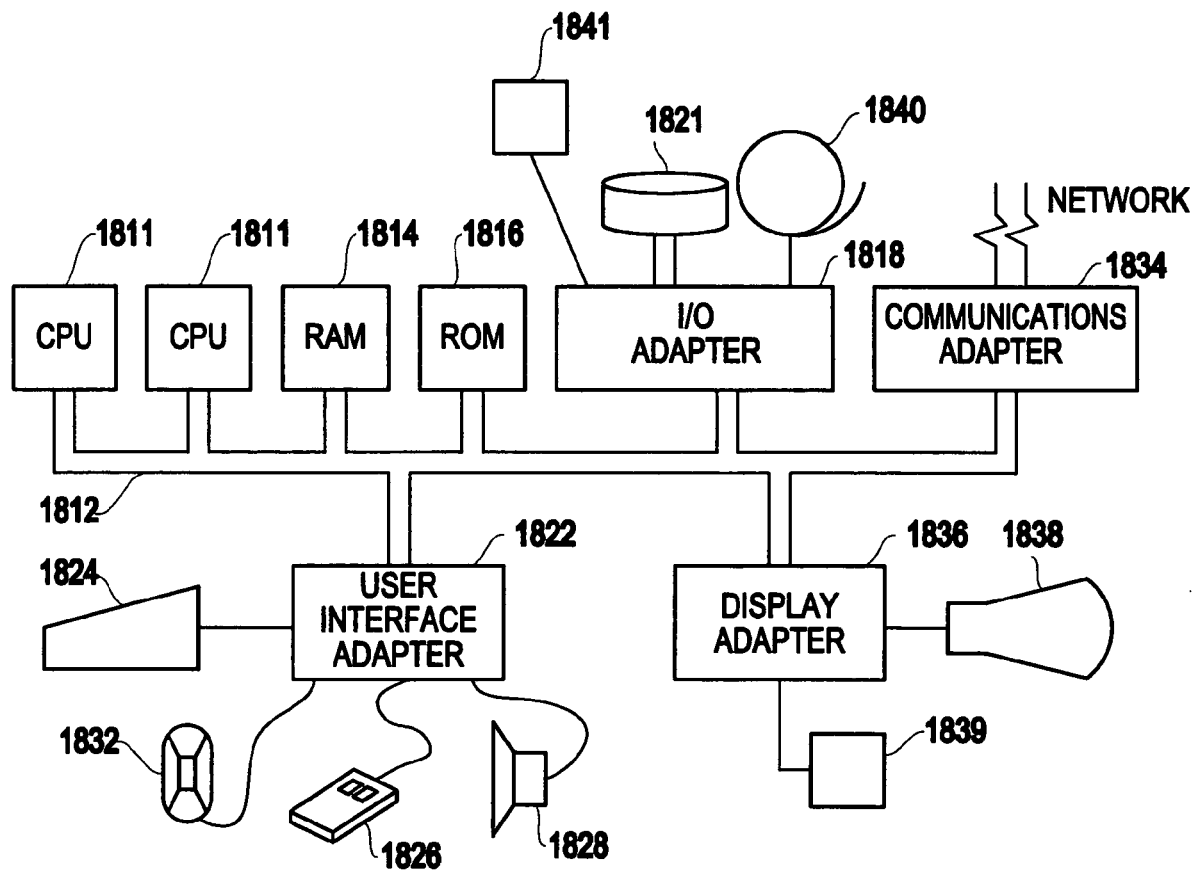
FIG. 18 illustrates a typical hardware configuration which may be used to implement the inventive system and method for spatially profiling a hydrophobicity distribution for a transmembrane protein, according to an exemplary embodiment of the present invention.

Referring now to FIG. 18, system 1800 illustrates a typical hardware configuration which may be used to implement the inventive system and method for spatially profiling a hydrophobicity distribution for a transmembrane protein. The configuration has preferably at least one processor or central processing unit (CPU) 1811. The CPUs 1811 are interconnected via a system bus 1812 to a random access memory (RAM) 1814, read-only memory (ROM) 1816, input/output (I/O) adapter 1818 (for connecting peripheral devices such as disk units 1821 and tape drives 1840 to the bus 1812), user interface adapter 1822 (for connecting a keyboard 1824, mouse 1826, speaker 1828, microphone 1832, and/or other user interface device to the bus 1812), a communication adapter 1834 for connecting an information handling system to a data processing network, the Internet, and Intranet, a personal area network (PAN), etc., and a display adapter 1836 for connecting the bus 1812 to a display device 1838 and/or printer 1839. Further, an automated reader/scanner 1841 may be included. Such readers/scanners are commercially available from many sources.

In addition to the system described above, a different exemplary aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this exemplary aspect of the present invention is directed to a programmed product, including signal-bearing media tangibly embodying a program of machine-readable instructions executable by a digital data processor to perform the above method.

Such a method may be implemented, for example, by operating the CPU 1811 to execute a sequence of machine-readable instructions. These instructions may reside in various types of signal bearing media.

Thus, this exemplary aspect of the present invention is directed to a programmed product, comprising signal-bearing media tangibly embodying a program of machine-readable instructions executable by a digital data processor incorporating the CPU 1811 and hardware above, to perform the method of the invention.

Figure 19:
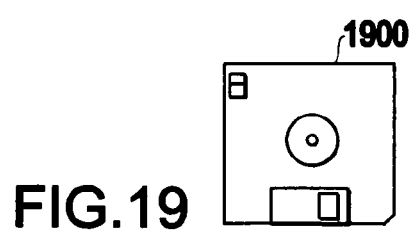
FIG. 19 illustrates a programmable storage medium which may be used to perform a method for spatially profiling a hydrophobicity distribution for a transmembrane protein, according to an exemplary embodiment of the present invention.

This signal-bearing media may include, for example, a RAM contained within the CPU 1811, as represented by the fast-access storage for example. Alternatively, the instructions may be contained in another signal-bearing media, such as a magnetic data storage diskette 1900 (FIG. 19), directly or indirectly accessible by the CPU 1811.

Whether contained in the computer server/CPU 1811, or elsewhere, the instructions may be stored on a variety of machine-readable data storage media, such as DASD storage (e.g, a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch"cards, or other suitable signal-bearing media including transmission media such as digital and analog and communication links and wireless. In an illustrative embodiment of the invention, the machine-readable instructions may comprise software object code, complied from a language such as C+, C++ etc.

With its unique and novel features, the present invention provides a system and method which enables a determination of the spatial distribution of hydrophobicity over an entire multimeric extent, not only in the region proximate to the protein lipid interface.

While the invention has been described in terms of one or more exemplary embodiments, those skilled in the art will recognize that the invention can be practiced with modification within the spirit and scope of the appended claims. Specifically, one of ordinary skill in the art will understand that the drawings herein are meant to be illustrative, and the design of the inventive assembly is not limited to that disclosed herein but may be modified within the spirit and scope of the present invention.

Further, Applicant's intent is to encompass the equivalents of all claim elements, and no amendment to any claim the present application should be construed as a disclaimer of any interest in or right to an equivalent of any element or feature of the amended claim.

What is claimed is:

1. A system for spatially profiling a hydrophobicity distribution for a transmembrane protein, said system comprising:
   a scaler which generates scaled hydrophobicity values for said transmembrane protein;
   a profiler which spatially profiles a hydrophobicity distribution for said transmembrane protein based on said scaled hydrophobicity value; and a display device for displaying output of said profiler,
   wherein said profiler generates a hydrophobicity distribution profile for said protein using a predetermined profiling geometry which is selected to approximate an external shape of said protein within a lipid bilayer, and wherein said profiler comprises:
an identifier for identifying a residue external to said membrane and removing said residue to obtain a truncated structure comprising plural residue side-chains which are internal to said membrane; and
a calculator which:
calculates plural residue centroids for said plural residue side-chains;
calculates a distribution of said plural residue centroids using a series of nested shapes which are consistent with said profiling geometry and provide contours about an axis that correlate with a lipid exposure for the residues proximate to a boundary between said protein and said lipid bilayer; and
obtains a geometric center for said distribution of said plural residue centroids, said hydrophobicity profile being about said axis through said geometric center and normal to a plane of said membrane.

2. The system according to claim 1, wherein said scaled hydrophobicity values comprise shifted and scaled hydrophobicity values of residue hydrophobicity.

3. The system according to claim 1, wherein said profiler spatially profiles said hydrophobicity distribution over a spatial extent of said transmembrane protein.

4. The system according to claim 1, wherein said scaled hydrophobicity values are derived from data pertaining to a structure of said transmembrane protein.

5. The system according to claim 1, wherein said identifier identifies a residue external to said membrane, using at least one of hydrophobicity sliding window analysis and visual inspection.

6. The system according to claim 5, wherein said profiler further comprises a residue remover which removes said residue to obtain said truncated structure.

7. The system according to claim 1, wherein a structure of said transmembrane protein is asymmetrical about said axis, and said predetermined profiling geometry comprises an elliptical cylinder.

8. The system according to claim 7, wherein said scaler scales said hydrophobicity values to obtain said scaled hydrophobicity values, using a scale that segregates amino acid values of hydrophobicity into a polar, polar uncharged and polar charged residues.

9. The system according to claim 8, wherein said scaler shifts said scaled hydrophobicity values to provide shifted and scaled values having a value of zero hydrophobicity when a predetermined number of residues of each truncated structure are collected, said shifted and scaled values being scaled to provide a standard deviation of unity for each truncated structure.

10. The system according to claim 9, wherein said profiler accumulates said shifted and scaled values of residue hydrophobicity as a function of an increasing size of each nested shape of a profiling geometry until a largest shape encapsulates a predetermined number of the residues, to generate an accumulated spatial distribution of residue hydrophobicity given by a function H(d) which is a sum of residue hydrophobicity values within the circular, elliptical or conical cylinder of radius d.

11. The system according to claim 10, wherein said profiler obtains a hydrophobicity profile by calculating the values of H(d).

12. The system according to claim 11, wherein if H(d) increases, the average hydrophobic value of the residues collected over a shell of width one or more Angstroms is greater than the average value of residue hydrophobicity for the entire structure, and
wherein if H(d) decreases, the average hydrophobic value of the residues collected over a shell of width one or more Angstroms is less than the average value of residue hydrophobicity for the entire structure.

13. The system according to claim 10, wherein said accumulated spatial distribution comprises a set of sequential values of accumulated residue hydrophobicity with increasing distance from a center of the structure to the protein/lipid interface within a bilayer, said set of sequential values comprising a zero-order moment profile of the residue hydrophobicity from the interior to the exterior of the structure.

14. The system according to claim 1, further comprising:
a database which stores data pertaining to a structure of said transmembrane protein; and
an input device for inputting and manipulating said data.

15. A method of spatially profiling a hydrophobicity distribution for a transmembrane protein, said method comprising:
scaling hydrophobicity values for said transmembrane protein to generate scaled hydrophobicity values;
spatially profiling a hydrophobicity distribution for said transmembrane protein based on said scaled hydrophobicity values; and a display device for displaying output of said profiler,
wherein said spatially profiling comprises generating a hydrophobicity distribution profile for said protein using a predetermined profiling geometry which is selected to approximate an external shape of said protein within a lipid bilayer, said generating said hydrophobicity distribution profile comprising:
identifying a residue external to said membrane and removing said residue to obtain a truncated structure comprising plural residue side-chains which are internal to said membrane;
calculating plural residue centroids for said plural residue side-chains;
calculating a distribution of said plural residue centroids using a series of nested shapes which are consistent with said profiling geometry and provide contours about an axis that correlate with a lipid exposure for the residues proximate to a boundary between said protein and said lipid bilayer; and
obtaining a geometric center for said distribution of said plural residue centroids, said hydrophobicity profile being about said axis through said geometric center and normal to a plane of said membrane.

16. The method according to claim 15, wherein said identifying a residue external to said membrane, comprises using hydrophobicity sliding window analysis and visual inspection.

17. The method according to claim 15, wherein said scaling said hydrophobicity values comprises scaling hydrophobicity values to obtain said scaled hydrophobicity values, using a scale that similarly segregates amino acid values of hydrophobicity into a polar, polar uncharged and polar charged residues.

18. The method according to claim 17, wherein said scaling said hydrophobicity values further comprises shifting said scaled hydrophobicity values to provide shifted and scaled values having a value of zero hydrophobicity when a predetermined number of residues of each truncated structure are collected, said shifted and scaled values being scaled to provide a standard deviation of unity for each truncated structure.

19. The method according to claim 18, wherein said spatially profiling further comprises accumulating said shifted and scaled values of residue hydrophobicity as a function of increasing size of each nested shape of the profiling geometry until a largest shape encapsulates a predetermined number of the residues, to generate an accumulated spatial distribution of residue hydrophobicity given by the function H(d) which is the sum of the values of residue hydophobicity within the circular, elliptical or conical cylinder of radius d.

20. The method according to claim 19, wherein said spatially profiling further comprises obtaining a hydrophobicity profile by calculating the values of H(d).

21. The system according to claim 1, wherein said scaled hydrophobicity values comprise information regarding a proposed three-dimensional transmembrane structure of said transmembrane protein.

22. The system according to claim 21, wherein said profiler profiles said hydrophobicity distribution for said transmembrane protein to validate said proposed three-dimensional transmembrane structure.

\* \* \* \* \*